United States Patent
Demas et al.

(10) Patent No.: US 9,724,473 B2
(45) Date of Patent: Aug. 8, 2017

(54) MULTI-DIRECTIONAL LOW-DISPLACEMENT FORCE SENSOR

(71) Applicant: Nickolas Peter Demas, Cambridge, MA (US)

(72) Inventors: Nickolas Peter Demas, Cambridge, MA (US); Ian W. Hunter, Lincoln, MA (US); Michael Thomas Nawrot, Somerville, MA (US); Brian Hemond, Cambridge, MA (US)

( * ) Notice: Subject to any disclaimer, the term of this patent is extended or adjusted under 35 U.S.C. 154(b) by 0 days.

(21) Appl. No.: 14/993,345

(22) Filed: Jan. 12, 2016

(65) Prior Publication Data

US 2017/0197032 A1    Jul. 13, 2017

(51) Int. Cl.
- *G01B 7/16* (2006.01)
- *A61M 5/30* (2006.01)
- *G01L 5/16* (2006.01)
- *G01L 5/00* (2006.01)

(52) U.S. Cl.
CPC ............. *A61M 5/30* (2013.01); *G01L 5/0038* (2013.01); *G01L 5/161* (2013.01); *A61M 2205/332* (2013.01)

(58) Field of Classification Search
CPC . A61M 5/30; A61M 2205/332; G01L 5/0038; G01L 5/161
USPC .................................... 73/760, 774, 862.044
See application file for complete search history.

(56) References Cited

U.S. PATENT DOCUMENTS

| | | | | |
|---|---|---|---|---|
| 5,147,311 A | * | 9/1992 | Pickhard | A61M 5/148 604/131 |
| 5,352,194 A | * | 10/1994 | Greco | A61M 1/008 600/579 |
| 5,913,455 A | * | 6/1999 | La | B05C 5/0225 222/146.5 |
| 8,105,270 B2 | * | 1/2012 | Hunter | A61B 5/0051 604/65 |
| 8,740,838 B2 | * | 6/2014 | Hemond | A61M 5/30 604/503 |
| 8,776,616 B2 | * | 7/2014 | Szasz | G01L 5/161 73/862.044 |
| 9,486,589 B2 | * | 11/2016 | Hunter | A61M 5/16859 |
| 2012/0003601 A1 | * | 1/2012 | Hunter | A61C 19/063 433/27 |
| 2012/0065615 A1 | * | 3/2012 | Boyd | A61M 5/30 604/500 |
| 2014/0142507 A1 | * | 5/2014 | Armes | A61M 5/3287 604/112 |

* cited by examiner

*Primary Examiner* — Max Noori

(57) ABSTRACT

A device for the measurement of forces on the tip of a jet injector drug ampoule. Sensor consists of multiple spokes with strain sensing capability where each spoke has a modified linkage to allow for quasi-free bending behavior on one spoke end. By using the strain output of all three full bridges in parallel, it is possible to discriminate between lateral forces and axial forces directed collinear with the center axis of the ampoule applied to the tip of the nozzle. This information can be relayed to the user to attain, for example, a pre-determined contact force between the nozzle and an area receiving an injection.

49 Claims, 14 Drawing Sheets

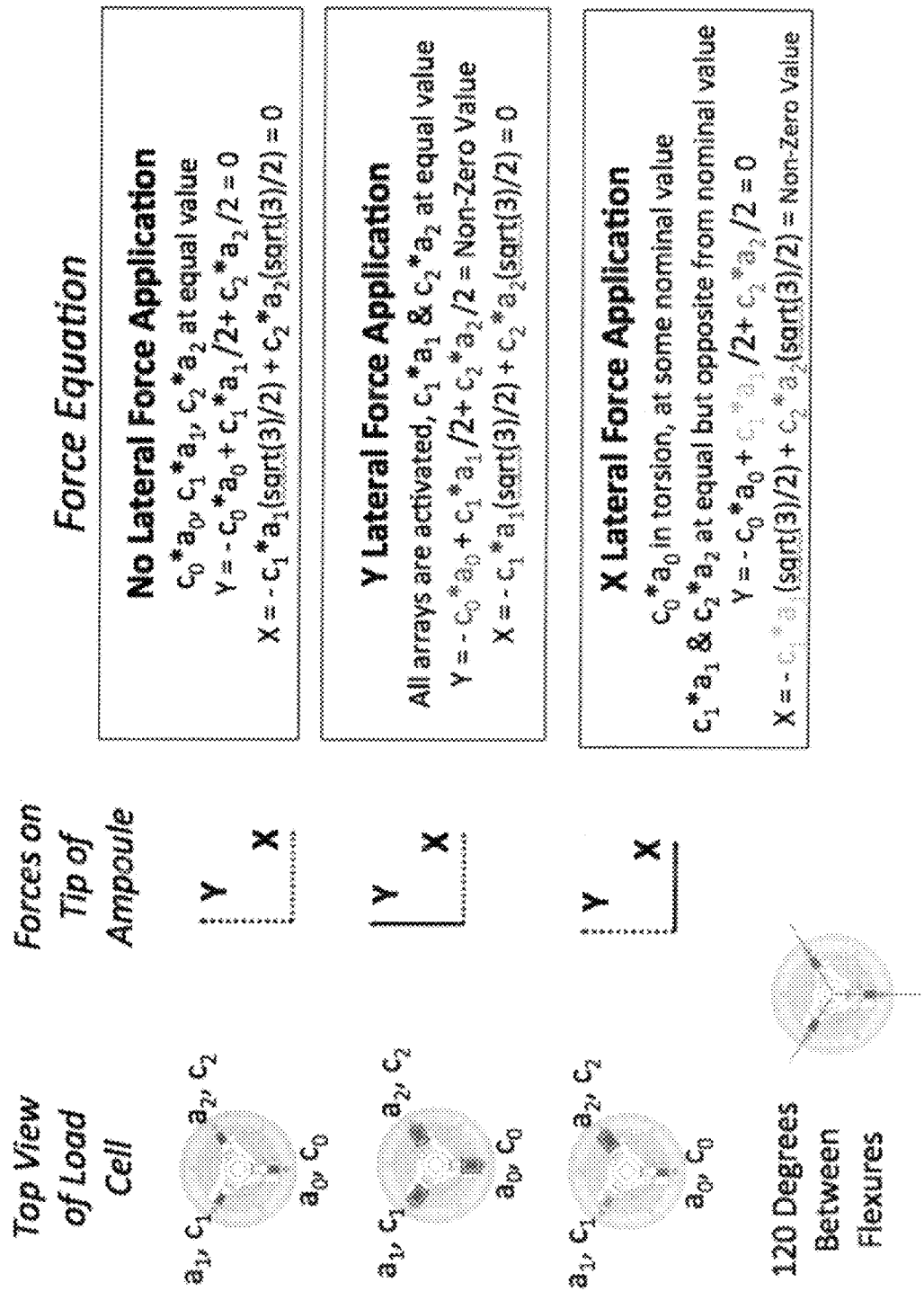

MULTI-DIRECTIONAL LOW-DISPLACEMENT FORCE SENSOR

BACKGROUND

Needle-free injectors (NFIs) operate by creating a high pressure jet of fluid/powder that penetrates the skin. Delivery is rapid (typically <0.5 s) which reduces apprehension while enhancing patient acceptance and ultimately compliance. In addition, NFIs have been shown to improve the efficacy of certain medications (Taylor et al. 1981; Jackson et al. 2001; Williams et al. 2000). Several needle-free injectors use springs or compressed inert gases to propel fluid through the skin and into the underlying tissue. This affords minimal control over the pressure applied to the drug during the time course of the injection, parameters shown to be integral to determining the depth and dispersion of drug delivered (Wendell et al. 2006; Shergold et al. 2006), and hence its absorption into the circulation. Others have incorporated some pressure pulse shaping by using variable orifice gas valves or fast/slow pyrotechnic charges. More recently, Stachowiak et al. (2009) have used piezoelectric actuators for dynamic control of delivery, accomplished at the expense of a limited piston stroke and volume of fluid delivered. An alternative approach to jet drug delivery is to store energy in electrical form and impose a time varying pressure profile (waveform) on the drug volume through the use of a monitored and servo-controlled electromechanical actuator such as a linear Lorentz-force actuator. Needle-free injectors may include sensors that can be used to control the actuator.

There are a great many multi-axis force sensors utilizing the measurement of strain to discern the magnitude and direction of an applied force. Most multi-axis force sensors however have assemblies that require a significant length available in the axial direction to be implemented, are difficult/costly to manufacture, have an unnecessarily redundant number of locations in which strain is measured, cannot have a drug ampoule of a needle-free injector mounted to them (and associated piston pass through them), result in significant displacements when loaded (of which a subsequent problem is inaccuracy in the injected volume or misalignment between the piston and the rest of the ampoule), have flexures that are limited to exactly twice the length of the sensing element to produce maximum signal which increases the overall radius required of the device, or have not been reduced to practice for measuring forces on the nozzle of a jet injector drug delivery ampoule assembly.

SUMMARY

The present invention relates to the measurement of multi-axis forces with low resulting displacements to enable the measurement and monitoring, but more particularly, but not exclusively, to the measurement and monitoring of forces on the nozzle of a jet injector drug delivery ampoule assembly in contact with a surface receiving an injection. In one embodiment, the sensor uses aluminum as the flexure substrate material, which is shaped to induce a more favorable stress distribution which can be measured using polyamide-backed resistive strain gauges. Using FR-4 grade glass-reinforced epoxy laminate ("FR-4") as the flexure material, for example, can enable the force sensor to be more easily mass manufactured using common printed circuit board (PCB) fabrication techniques. Further, using FR-4, one can employ printed resistive strain gauges or mounted semiconductor strain sensors to measure lateral and normal forces applied to the nozzle.

The techniques and designs of the current approach readily and simply overcome the limitations of prior approaches. For example, a sensor of the present invention may be relatively thin in the axial direction (allowing for the smallest amount of length added to the entire jet injector device), be readily manufactured with well-known techniques and requires few parts requiring assembly, function with three flexures and associated sensing arrays to measure forces applied both laterally and normally to the nozzle while reducing the number of strain regions requiring measurement, readily have a drug ampoule mounted to it (and associated piston pass through it), result in extremely minor displacements when loaded (of which a subsequent feature is little error induced in the injected volume), have flexures that may be shorter than twice the length of the sensing element to produce maximum signal by incorporating quasi-free boundary condition elements, and be used for measuring forces on the nozzle of a jet injector drug delivery ampoule assembly. The sensing arrays are preferably formed by full bridge resistive gauge circuits on each of three spokes that connect the outer fixed portion to the inner sensing portion to improve the output signal for small forces that induce small deflections, as well as reject measurement of bending in the lateral direction, twisting, and temperature effects. These features result in a multi-axis force sensor for jet injection that exhibits very low displacements when forces are applied. Additional benefits of using a force sensor of the present approach in a jet injector are better control of injection depth and volume of injected substance, which can result in decreased pain and better dosage control. Further, embodiments of the invention can reduce the risk of accidental injections, for example, by enabling a lock-out feature when the force applied to the nozzle of the jet injector ampoule falls outside a predetermined range.

Sensing methods and devices of the invention provide a new and improved method or technique of and structures for attaining the above-described novel features while obviating the limitations of prior electro-mechanical devices of this type. Through the provision of sensitive strain sensing elements mounted on the top and bottom surface of flexural spokes, with a quasi-free boundary condition feature allowing for larger zones (than would be observed in a fixed-fixed flexural spoke construction) on the top and bottom of each flexural spoke (where compression or tension are observed when forces are applied to the inner sensing portion), larger fully compressive and fully tensile zones allow for strain sensing elements to interact with larger surfaces. Therefore, sensors of the current approach can output more substantial signals and make sensing multi-axis forces with smaller resulting displacements possible. Another advantage of the current approach is that it allows the compressive and tensile zones to be larger for a given flexure length, so that the lengths of the flexures can be shorter to decrease the total outer diameter of the force sensor.

Embodiments of the invention provide a method in which an ampoule may be mounted to a jet injector, allowing for force readings to be measured before the device comes into contact with the injection area, while the device is in contact with the injection area before the injection, and during the injection to measure pressure within the ampoule.

In one example, a device is described that can be made with full bridge resistive strain gauge arrays on each flexural spoke to maximize output signal from bending in the vertical direction and minimize output signal from bending in the horizontal direction, twisting, or temperature fluctuations.

BRIEF DESCRIPTION OF THE DRAWINGS

The present invention can best be understood in conjunction with the accompanying drawings, in which:

FIG. 21 illustrates top views of an example force sensor, forces on the tip of an ampoule, and associated equations.

Figure 1:
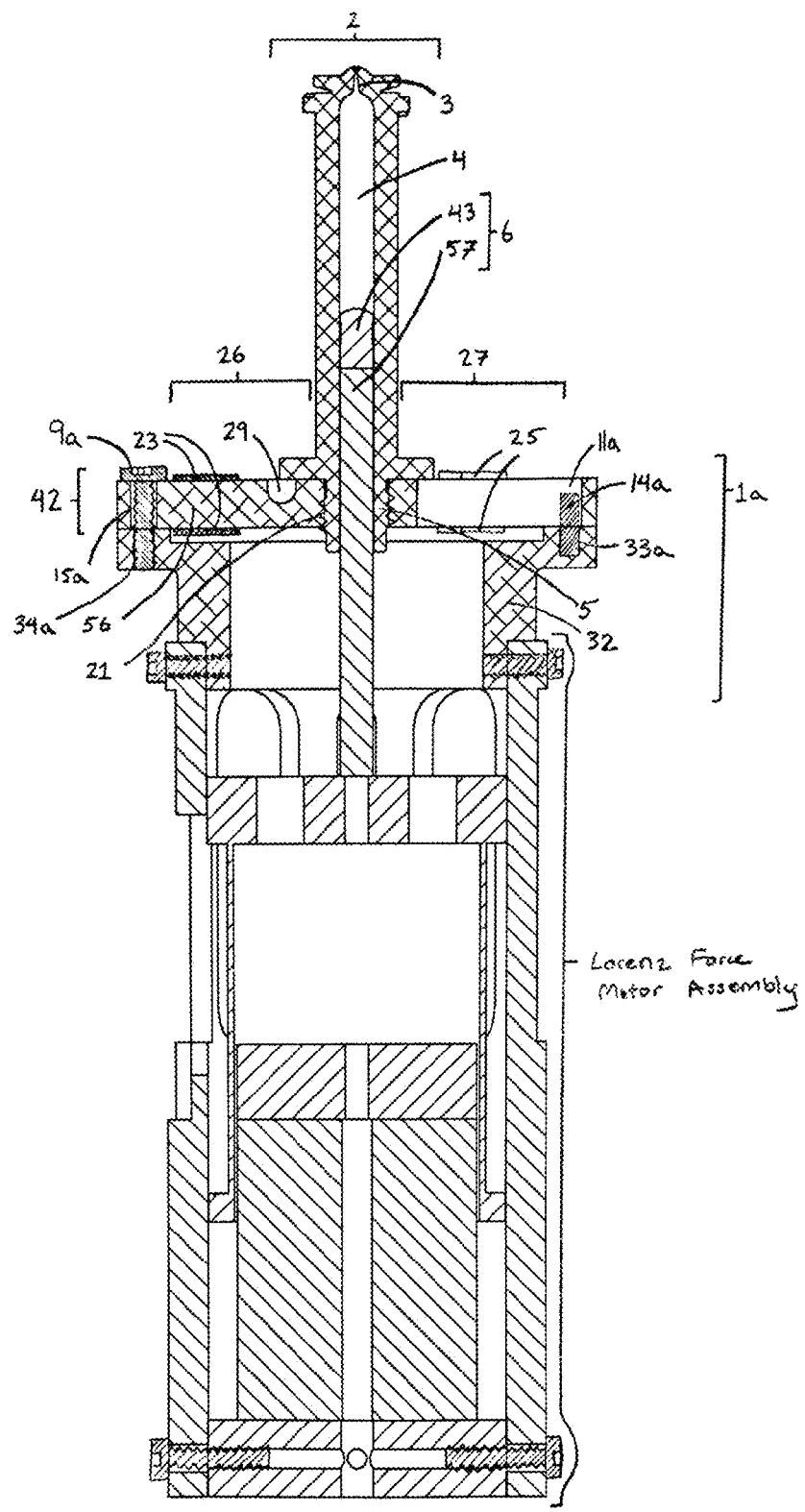
FIG. 1 is a sectional view of a jet injector device including a force sensor according to an embodiment of the invention.

In the drawings, preferred embodiments of the invention are illustrated by way of example, it being expressly understood that the description and drawings are only for the purpose of illustration and preferred designs, and are not intended as a definition of the limits of the invention.

DETAILED DESCRIPTION

A description of example embodiments of the invention follows.

FIG. 1 is a sectional view of an example jet injector device including a force sensor according to an embodiment of the invention. A force sensor [1a] is coupled to ampoule assembly [2] and mounted to a Lorentz-force motor assembly via adapter [32]. As shown, the adapter [32] is bolted to a housing of the Lorentz-force motor assembly, which includes a controllable magnet and coil electromagnetic actuator. The controllable actuator is coupled to piston [6] to drive the piston to, for example, eject a substance from inner volume [4] through nozzle [3] of the ampoule assembly. Further details of sensor [1a] and ampoule assembly [2] are described below in reference to FIGS. 2A-2B.

Jet injector devices that include Lorentz-force actuators and that are suitable for use with force sensors described in this disclosure are described in U.S. Pat. No. 7,833,189 ("Controlled needle-free transport") to Hunter et al., U.S. Pat. No. 8,172,790 (Needle-free injector device with auto-loading capability") to Hunter et al., and U.S. Pat. No. 8,740,838 ("Injection methods using a servo-controlled needle-free injector") to Hemond et al., the teachings of which are incorporated herein by reference in their entirety.

Figure 2A:
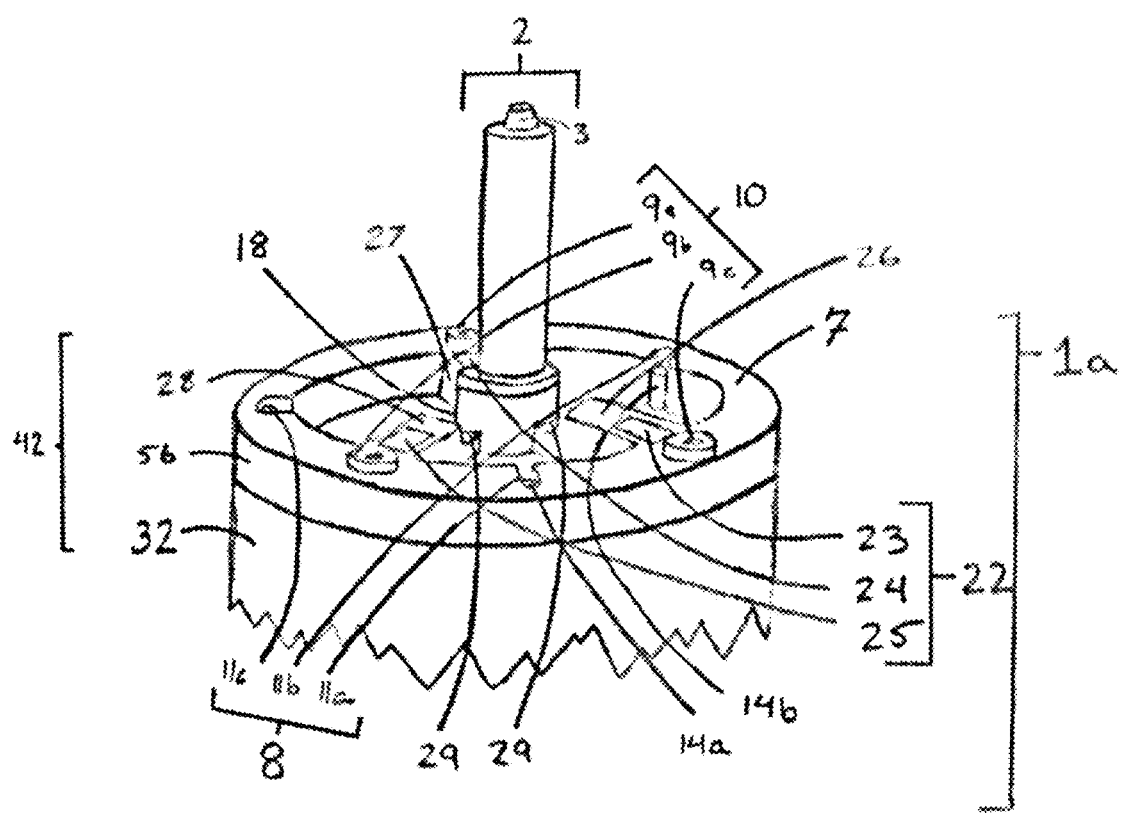
FIG. 2A is an isometric view of a fully assembled force sensor with an ampoule.

FIG. 2A is an isometric view of a fully assembled force sensor with an ampoule. The figure illustrates the following components:

Jet injector drug delivery ampoule assembly [2], which includes:

Nozzle [3], and other components not specifically shown; is mounted to;

Metal-based jet injector force sensor [1a], which includes:

Sensing assembly [42], which includes:

Metal base [56], which includes:

Outer fixed portion [7];

First flexural spoke [26], Second flexural spoke [27], and Third flexural spoke [28], each of which has formed in it:

Quasi-free boundary condition feature [29], e.g., a notch, a cut-out, or other features that provides a region of reduced thickness of the spoke;

Inner sensing portion [18];

Constraint features [8], which includes:

Locating slot one [11a], Locating slot two [11b], and Locating slot three [11c] in this embodiment;

Securing features [10], on the Metal base [56], including:

Through hole one [15a], Through hole two [15b], and Through hole three [15c] (see FIG. 2B) through which Bolt one [9a], Bolt two [9b], and Bolt three [9c], connect the Metal base [56] to the Adapter [32] which mounts to the jet injector housing in a preferred embodiment;

Sensor array [22], which includes:

First strain sensor [23], Second strain sensor [24], and Third strain sensor [25]

Adapter [32], which includes:
  Hole one [33a], Hole two [33b], and Hole three [33c] (see FIG. 2B) which align with Locating slot one [11a], Locating slot two [11b], and Locating slot three [11c];
  Threaded hole one [34a], Threaded hole two [34b], and Threaded hole three [34c] (see FIG. 2B) to which Bolt one [9a], Bolt two [9b], and Bolt three [9c], connect the Metal base [56] to the Adapter [32].
The adapter may include features to connect the adapter to the jet injector housing in a preferred embodiment, as illustrated in FIG. 1.
Locating pin one [14a], Locating pin two [14b], and Locating pin three [14c] which fit into Hole one [33a], Hole two [33b], and Hole three [33c] which align with Locating slot one [11a], Locating slot two [11b], and Locating slot three [11c] on the Metal base [56];
Bolt one [9a], Bolt two [9b], and Bolt three [9c], connect the Metal base [56] to the Adapter [32]

Forces applied to the tip of the Jet injector drug delivery ampoule assembly [2] deform First flexural spoke [26], Second flexural spoke [27], and/or Third flexural spoke [28]. These deformations are measured by the First strain sensor [23], Second strain sensor [24], and Third strain sensor [25]. The Quasi-free boundary condition feature [29] found on each of the flexural spokes [26, 27,28] increases the area of the Fully compressive zone [30] (not shown in FIG. 1) and Fully tensile zone [31] (not shown in FIG. 1) found on the top and bottom of each of the flexural spokes [26, 27, 28] allowing for larger strain sensors [23, 24, 25] and therefore more substantial measurements than if the Quasi-free boundary condition feature [29] found on each of the flexural spokes [26, 27, 28] was not present.

Figure 2B:
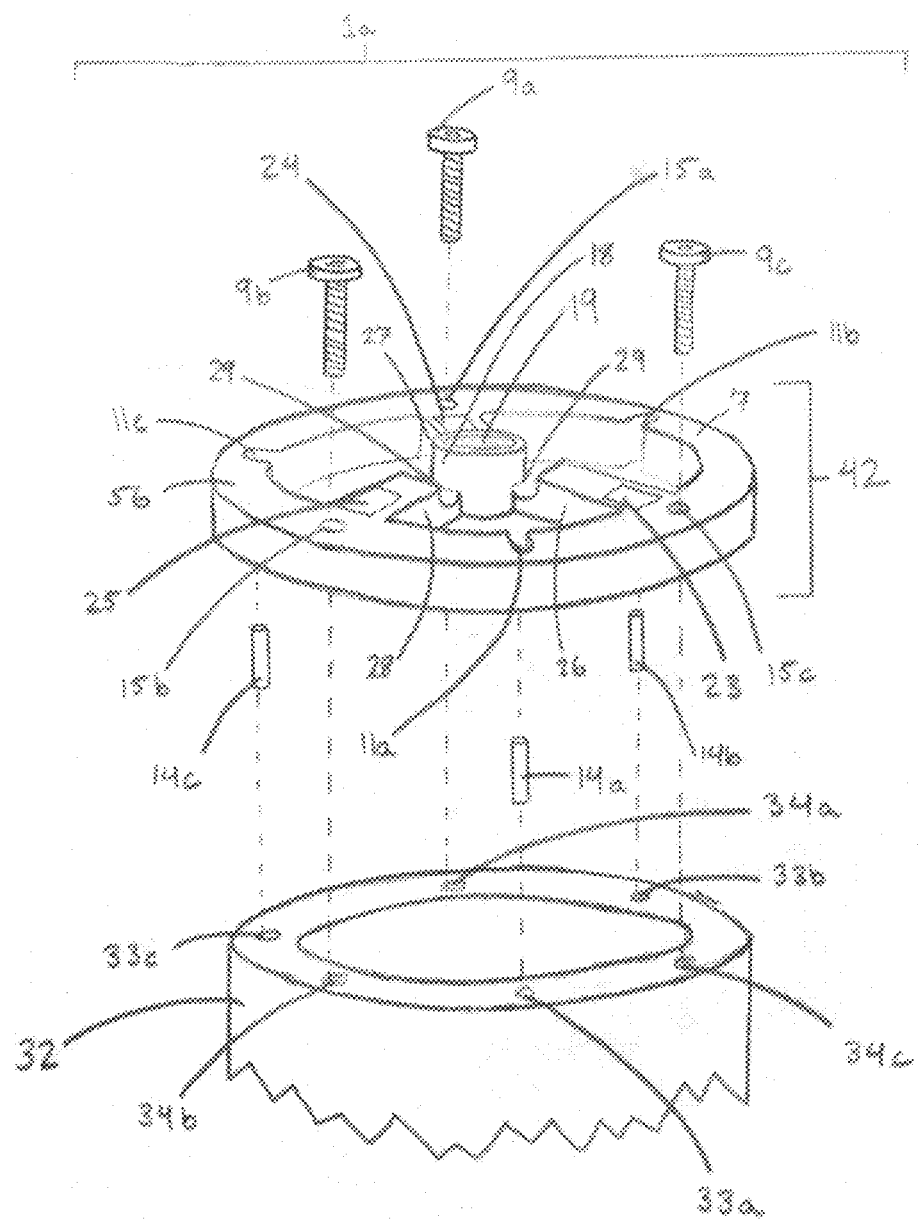
FIG. 2B is an isometric exploded view of the force sensor of FIG. 2A without the ampoule.

FIG. 2B is an isometric exploded view of Metal-based jet injector force sensor [1a] without the ampoule. It includes the following components:
Metal-based jet injector force sensor [1a], which includes:
  Sensing assembly [42], which includes:
    Metal base [56], which includes:
      Outer fixed portion [7], which is the portion of the Metal base [56] that contacts the Adapter [32];
      First flexural spoke [26], Second flexural spoke [27], and Third flexural spoke [28], each of which has formed in it:
        Quasi-free boundary condition feature [29];
      Inner sensing portion [18], in which is formed:
        Ampoule connection location [19];
      Constraint features [8] (see FIG. 2A), which includes:
        Locating slot one [11a], Locating slot two [11b], and locating slot three [11c] in this embodiment;
      Securing features [10] (not specifically labeled), on the Metal base [56], including
        Through hole one [15a], Through hole two [15b], and Through hole three [15c] through which;
        Bolt one [9a], Bolt two [9b], and Bolt three [9c], connect the Metal base [56] to the Adapter [32] which mounts to the jet injector housing in a preferred embodiment;
    Sensor array [22] (see FIG. 2A), which includes:
      First strain sensor [23], Second strain sensor [24], and Third strain sensor [25]

Adapter [32], which includes:
  Hole one [33a], Hole two [33b], and Hole three [33c] which align with Locating slot one [11a], Locating slot two [11b], and locating slot three [11c];
  Threaded hole one [34a], Threaded hole two [34b], and Threaded hole three [34c] to which Bolt one [9a], Bolt two [9b], and Bolt three [9c], connect the Metal base [56] to the Adapter [32]
Locating pin one [14a], Locating pin two [14b], and Locating pin three [14c] which fit into Hole one [33a], Hole two [33b], and Hole three [33c] which align with Locating slot one [11a], Locating slot two [11b], and locating slot three [11c] on the Metal base [56];
Bolt one [9a], Bolt two [9b], and Bolt three [9c], connect the Metal base [56] to the Adapter [32]
The Jet injector drug delivery ampoule assembly [2] is not shown in FIG. 2B.
The exploded view of FIG. 2B shows how the components align and fit together in a preferred embodiment.

Figure 3A:
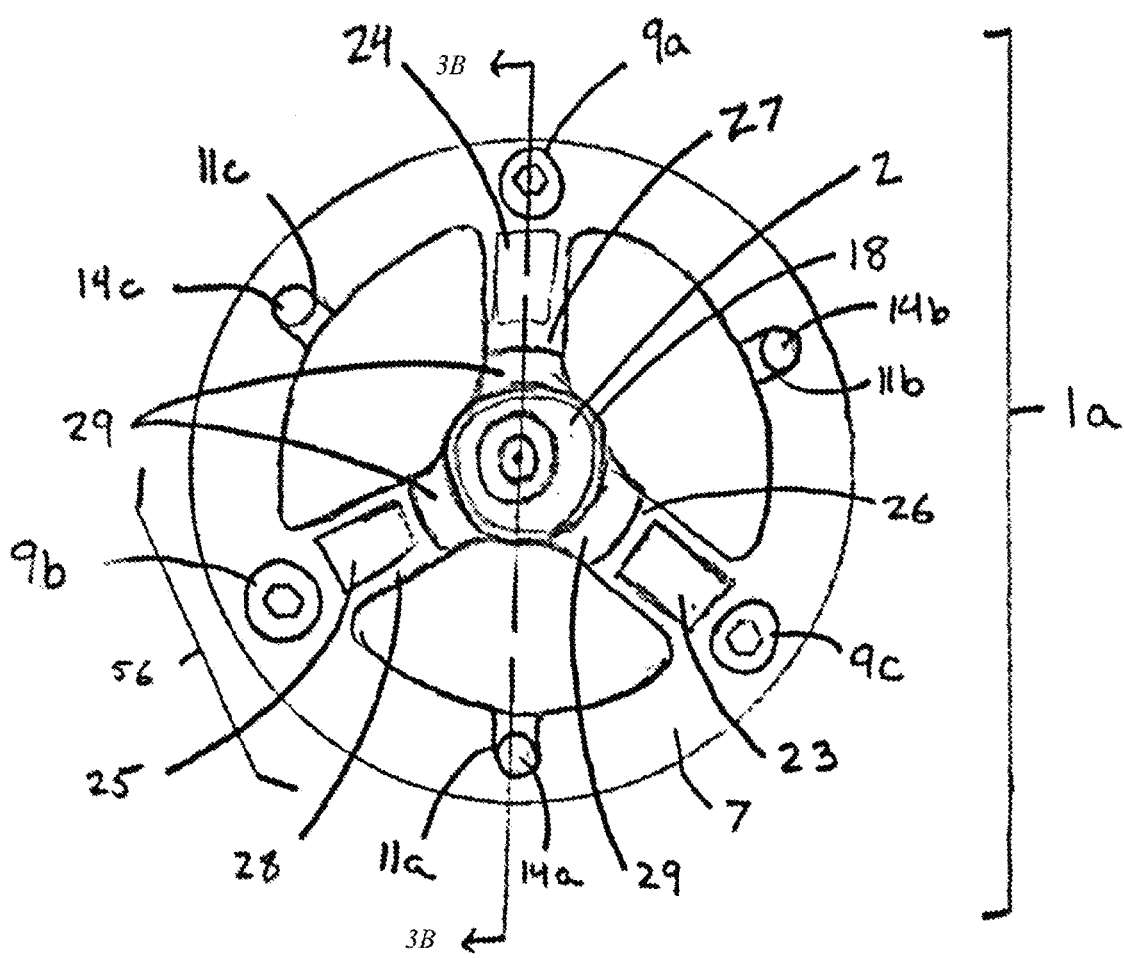
FIG. 3A is a top view of a fully assembled force sensor with an ampoule.

FIG. 3A is a top view of a fully assembled force sensor with an ampoule. FIG. 3A illustrates the following components:
Jet injector drug delivery ampoule assembly [2], is mounted to;
Metal-based jet injector force sensor [1a], which includes:
  Sensing assembly [42] (see FIG. 2A), which includes:
    Metal base [56], which includes:
      Outer fixed portion [7];
      First flexural spoke [26], Second flexural spoke [27], and Third flexural spoke [28], all of which has formed in it:
        Quasi-free boundary condition feature [29];
      Inner sensing portion [18];
      Constraint features [8] (FIG. 2A), which includes:
        Locating slot one [11a], Locating slot two [11b], and Locating slot three [11c];
      Securing features [10] (FIG. 2A), on the Metal base [56], include:
        Through hole one [15a], Through hole two [15b], and Through hole three [15c], (FIG. 2B) through which
          Bolt one [9a], Bolt two [9b], and Bolt three [9c] connect the Metal base [56] to the Adapter [32] (FIG. 2B) which mounts to the jet injector housing in a preferred embodiment;
    Sensor array [22] (FIG. 2A), which includes:
      First strain sensor [23], Second strain sensor [24], and Third strain sensor [25];
  Locating pin one [14a], Locating pin two [14b], and Locating pin three [14c], which fit into Hole one [33a], Hole two [33b], and Hole three [33c] (FIG. 2B), respectively, which align with Locating slot one [11a], Locating slot two [11b], and Locating slot three [11c], respectively, on the Metal base [56].

Figure 3B:
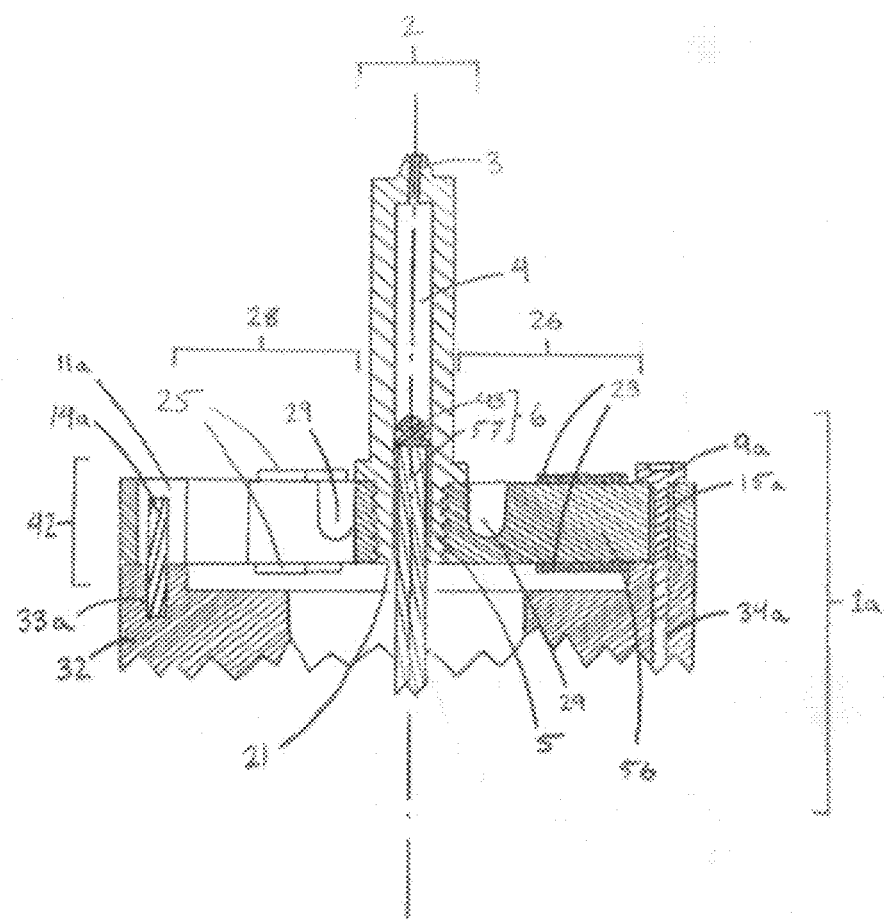
FIG. 3B is a cross-section view of a fully assembled force sensor with an ampoule.

FIG. 3B is a cross-section view of a fully assembled force sensor with an ampoule. The following components are illustrated:
Jet injector drug delivery ampoule assembly [2], which includes:
  Nozzle [3], Ampoule inner volume [4], threaded connector [5]
  and Piston [6], which, in a preferred embodiment, includes:
    Piston Tip [43] and Piston Shaft [57]
  is mounted to Metal-based jet injector force sensor [1a], which includes:
Sensing assembly [42], which includes:
Metal base [56], which includes:
Outer fixed portion [7] (not specifically labeled, but see FIG. 3A);
First flexural spoke [26], Second flexural spoke [27], and Third flexural spoke [28], of which a cross section view of First flexural spoke [26], and partial view of Third flexural spoke [28] are shown, each of which have formed in it:
Quasi-free boundary condition feature [29];
Inner sensing portion [18] (FIG. 3A), in which is formed:
Piston pass-through port [21] so that the piston can connect to the actuator of a jet injector in a preferred embodiment;
Constraint features [8] (FIG. 2A), which includes:
Locating slot one [11a], Locating slot two [11b], and Locating slot three [11c], of which a cross section view of Locating slot one [11a] is shown;
Securing features [10] (FIG. 2A), on the Metal base [56], including:
Through hole one [15a], Through hole two [15b], and Through hole three [15c], of which a cross section view of Through hole one [15a] is shown, through which
Bolt one [9a], Bolt two [9b], and Bolt three [9c] connect the Metal base [56] to the Adapter [32] which mounts to the jet injector housing in a preferred embodiment, of which a cross section view of Bolt one [9a] is shown;
Sensor array [22] (FIG. 2A), which includes:
First strain sensor [23], Second strain sensor [24], and Third strain sensor [25], of which a cross section view of First strain sensor [23], and partial view of Third strain sensor [25] is shown;
Adapter [32], which includes:
Hole one [33a], Hole two [33b], and Hole three [33c], of which a cross section view of Hole one [33a] is shown, which align with Locating slot one [11a], Locating slot two [11b], and Locating slot three [11c], of which a cross section view of Locating slot one [11a] is shown;
Threaded hole one [34a], Threaded hole two [34b], and Threaded hole three [34c], of which a cross section view of Threaded hole one [34a] is shown, to which Bolt one [9a], Bolt two [9b], and Bolt three [9c], respectively, connect the Metal base [56] to the Adapter [32], of which a cross section view of Bolt one [9a] is shown.
A method to connect the adapter to the jet injector housing in a preferred embodiment is illustrated in FIG. 1.
Locating pin one [14a], Locating pin two [14b], and Locating pin three [14c], of which a cross section view of Locating slot one [11a] is shown, fit into Hole one [33a], Hole two [33b], and Hole three [33c] respectively, of which a cross section view of Hole one [33a] is shown, and align with Locating slot one [11a], Locating slot two [11b], and locating slot three [11c], respectively of which a cross section view of Locating slot one [11a] is shown, on the Metal base [56].
The Piston [6] can actuate back and forth to draw in or expel fluid through the Nozzle [3]. The sensor can measure the force between the nozzle and the injection area it is contacting before the area requiring injection as well as measure the force exerted by the Piston [6] during the injection to measure pressure within the Ampoule inner volume [4].

Figure 3C:
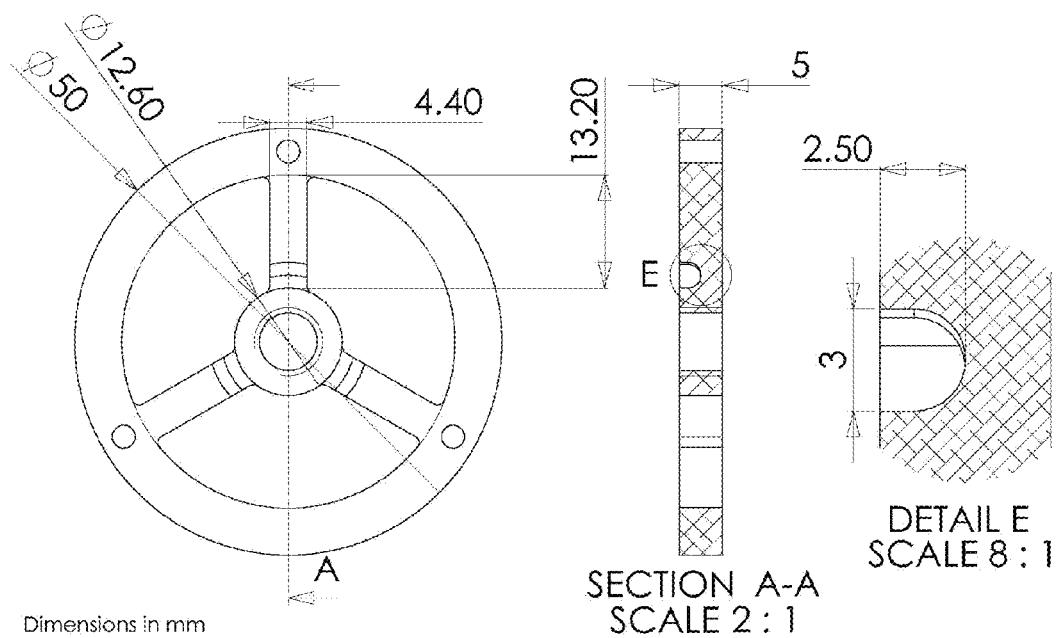
FIG. 3C illustrates a base of a sensor assembly.

FIG. 3C illustrates an example base of a sensor assembly. The figure provides a top view of the base, a sectional view of the base and a detail view of a notch in a flexural spoke of the base. The base includes an inner ring that is connected to an outer ring by three flexural spokes, each of which has formed in it a notch near the inner ring. The inner ring, outer ring and spokes can be integrally formed or machined from an aluminum substrate. In this example, the substrate is Al 7075-T651, the diameter of the inner ring is 12.60 mm, the diameter of the outer ring is 50 mm, and the length of each spoke is 13.20 mm. The base has a uniform thickness of 5 mm, except for the notches, which are formed in the top of the surface of the base to a depth of 2.5 mm, i.e., half the thickness of the base. As shown, each notch is 3 mm wide and is curved.

The design and dimensions of the three-spoke base of FIG. 3C are a result of a finite element analysis. Stress contributions were adjusted to be advantageous to the way force is measured. Because force is measured using gauges placed on the surface of the spokes, a design criterion included to maximize the sum total of compressive or tensile strain in the area covered by a single strain gauge, in order to make the sensor more sensitive.

Figure 4:
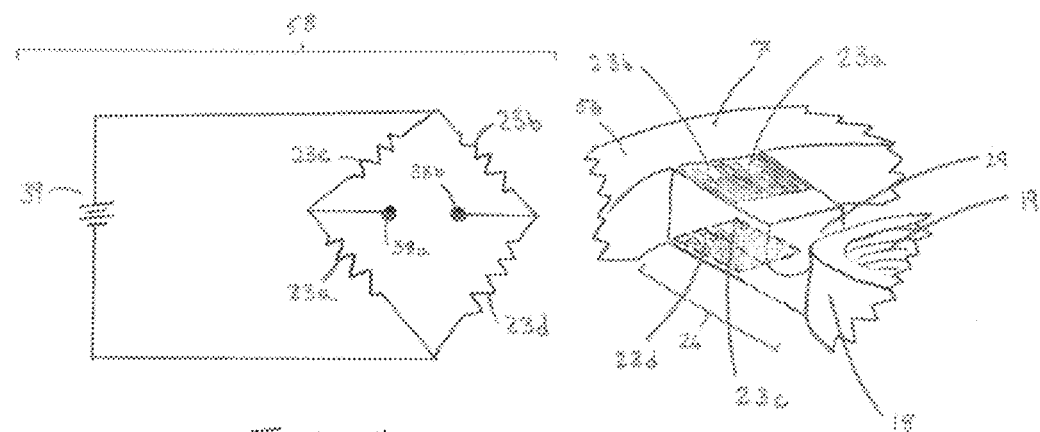
FIG. 4 illustrates (left panel) an electrical circuit diagram of a full-bridge sensor circuit and (right panel) an isometric view of a flexural spoke and associated sensor locations.

FIG. 4 illustrates an electrical circuit diagram (left panel) of the full-bridge sensor circuit and an isometric view (right panel) of the first flexural spoke and associated sensor locations.

With regard to the Electrical circuit [58], it includes:
Regulated voltage source [39];
Positive signal output [38a] and Negative signal output [38b];
First top strain gauge one [23a], First top strain gauge two [23b], First bottom strain gauge one [23c], and First bottom strain gauge two [23d] as shown. These gauges, in a preferred embodiment, are resistive strain sensors formed in flexible printed circuit board and mounted to the Metal base [56] but can also be semiconductor strain sensors. This configuration of gauges is duplicated on each flexural spoke using the same configuration of four strain gauges on each.
With regard to the isometric view of the first flexural spoke, it includes:
Metal base [56], which includes:
Outer fixed portion [7];
First flexural spoke [26], in which is formed:
Quasi-free boundary condition feature [29];
Inner sensing portion [18], in which is formed:
Ampoule connection location [19];
First top strain gauge one [23a], First top strain gauge two [23b], First bottom strain gauge one [23c], and First bottom strain gauge two [23d] fixed to the Metal base [56] as shown. These gauges, in a preferred embodiment, are resistive strain sensors formed in flexible printed circuit board and mounted to the Metal base [56] but can also be semiconductor strain sensors. This configuration of gauges is duplicated on each flexural spoke using the same configuration of four strain gauges on each.

An advantage of the strain gauge layout as shown in FIG. 4 is that the sensor is sensitive to axial direction deflection of the flexural spoke and insensitive to twisting of the spoke, lateral bending, overall compression or tension, and temperature variation. The full bridge sensor configuration includes four strain gauges that are active resistors. When the strain gauge is in compression, the resistance decreases. When the strain gauge is tension, the resistance increases. In the set-up shown in FIG. 4, the voltage between terminals [38a] and [38b] is proportional to the amount of strain. When a pulling force is applied to the spoke along its longitudinal axis (i.e., the axis through the center of the spoke in a direction from inner portion [18] to outer portion [7]), the resistance of all strain gauges increases and the measured voltage does to change. Twisting of the spoke along its longitudinal axis or sideways bending of the spoke also does not change the voltage at terminals [38a] and [38b], because the increase in resistance of some gauges cancels out the decreases in resistance of other gauges. Lateral bending also causes compressive and tensile loads to be placed on the gauges, but due to the wiring, the changes in resistance cancel and the lateral bending is rejected by the strain gauge array as shown in FIG. 4. Temperature variations that effect the entire strain gauge array cause all gauges to experience additional compression or tension, which is rejected by the wiring in FIG. 4.

The strain gauge layout and sensor configuration can measure axial force ($F_z$), along a major axis of the device, and lateral torques ($T_x$ and $T_y$). From the lateral torques the force at the tip of the ampoule, e.g., at the nozzle, can be calculated. Further details of the calculation of axial and lateral forces are described below in references to FIGS. 20 and 21.

Figure 5:
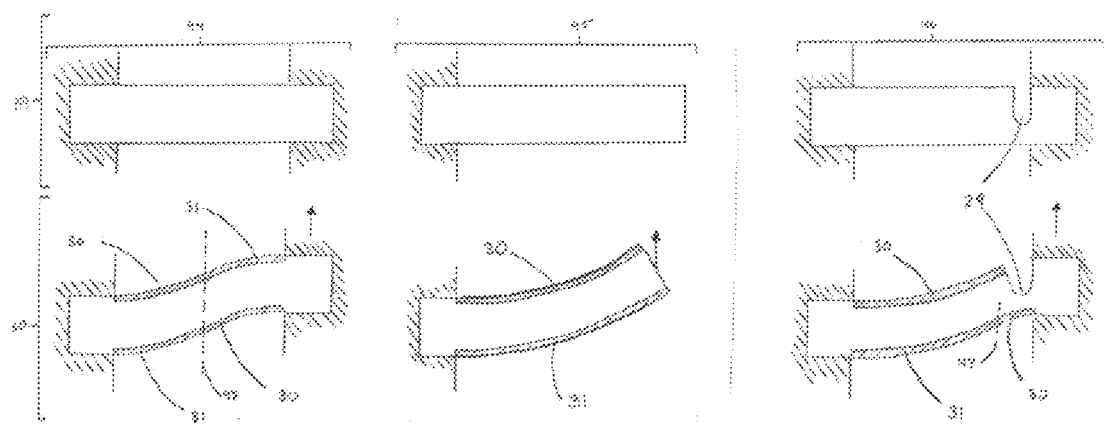
FIG. 5 illustrates beam bending fixed-fixed, fixed-free, and fixed-quasi-free states when loaded.

FIG. 5 illustrated beam bending in fixed-fixed, fixed-free, and fixed-quasi-free states when loaded. The figure illustrates the benefits of the Quasi-free boundary condition feature [29].

FIG. 5 shows Fixed/fixed flexural spoke configuration [44] in a Force-free state [59] and an Applied force state [60], whereby the arrow indicates the direction of force application, in the latter of which is observed:
  Fully compressive zone [30] on the top and bottom and a Fully tensile zone [31] on the top and bottom of the Fixed/fixed flexural spoke configuration [44] which are separated by a line indicating the Tension/compression transition [47]. The Fully compressive zone [30] and Fully tensile zone [31] occupy equal areas in a beam with a constant cross section when loaded in a Fixed/fixed flexural spoke configuration [44]. This limits the size of a displacement force sensor to exactly half of the length of the flexure for maximum signal output.

Also shown in FIG. 5 is Fixed/free flexural spoke configuration [45] in a Force-free state [59] and an Applied force state [60], whereby the arrow indicates the direction of force application, in the latter of which is observed:
  Fully compressive zone [30] on the top and a Fully tensile zone [31] on the bottom of the Fixed/free flexural spoke configuration [45]. There exists no Tension/compression transition [47] on the top or bottom surface. The Fully compressive zone [30] and Fully tensile zone [31] occupy the entire top and bottom surface respectively when loaded as shown, when a beam is loaded in a Fixed/free flexural spoke configuration [45]. This is suitable when comparing the available fully compressive or tensile areas to which a strain sensor may be mounted with the Fixed-fixed flexural spoke configuration, but is not appropriate for use in a force sensor for a jet injector as there is no mechanical connection to the Inner sensing portion [18] (FIGS. 2A, 4) to which a Jet injector drug delivery ampoule assembly [2] can be mounted.

FIG. 5 illustrates Fixed/quasi-free flexural spoke configuration [46] in a Force-free state [59] and an Applied force state [60], whereby the arrow indicates the direction of force application, in the latter of which is observed:
  Fully compressive zone [30] on the top and bottom and a Fully tensile zone [31] on the bottom of the Fixed/quasi-free flexural spoke configuration [46]. There exists no Tension/compression transition [47] on the top surface and, while a Tension/compression transition [47] exists on the bottom surface, it is skewed off center due to the Quasi-free boundary condition feature [29] which allows for a Fully tensile zone [31] to be much larger on the bottom surface than a Fully compressive zone [30]. This configuration increases the area occupied by the Fully compressive zone [30] on the top surface and Fully tensile zone [31] on the bottom surface, as compared to the Fixed/fixed flexural spoke configuration [44], to which a strain sensor may be mounted (to maximize output signal). Additionally, the Quasi-free boundary condition feature [29] allows for a mechanical connection to the Inner sensing portion [18] to which a Jet injector drug delivery ampoule assembly [2] can be mounted, as compared to the Fixed/free flexural spoke configuration [45] where such mounting was not possible.

Figure 6:
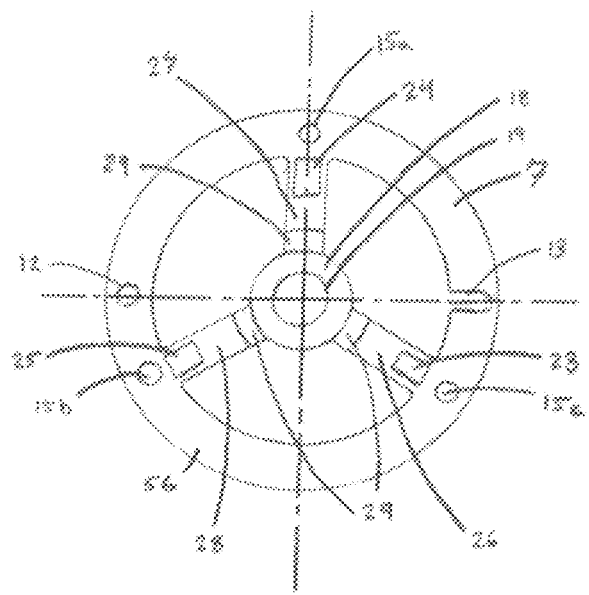
FIG. 6 shows a top view of a sensing assembly with an alternative constraint method using a slot and pin.

FIG. 6 shows a top view of the sensing assembly with an alternative constraint method using a slot and pin. The following components of the sensing assembly are shown:
  Metal base [56], which includes:
    Outer fixed portion [7];
    First flexural spoke [26], Second flexural spoke [27], and Third flexural spoke [28], each of which has formed in it:
      Quasi-free boundary condition feature [29];
    Inner sensing portion [18], in which is formed:
      Ampoule connection location [19];
    Constraint features [8], which includes:
      Locating hole [12] and Locating slot [13] in this alternate embodiment;
    Securing features [10] (FIG. 2A), which comprises on the Metal base [56] including:
      Through hole one [15a], Through hole two [15b], and Through hole three [15c] through which;
      Bolt one [9a], Bolt two [9b], and Bolt three [9c] (FIG. 2B), connect the Metal base [56] to the Adapter [32] (FIG. 2B) which mounts to the jet injector housing in a preferred embodiment;
  Sensor array [22] (FIG. 2B), which includes:
    First strain sensor [23], Second strain sensor [24], and Third strain sensor [25];
  Locating pin one [14a] and Locating pin two [14b] (FIG. 2A) which would fit into Locating hole [12] and Locating slot [13] to align the Sensing assembly [42] (FIG. 2A) to the Adapter [32] (FIG. 2B);

This configuration requires fewer features formed in the Metal base [56] and only two locating pins.

Figure 7:
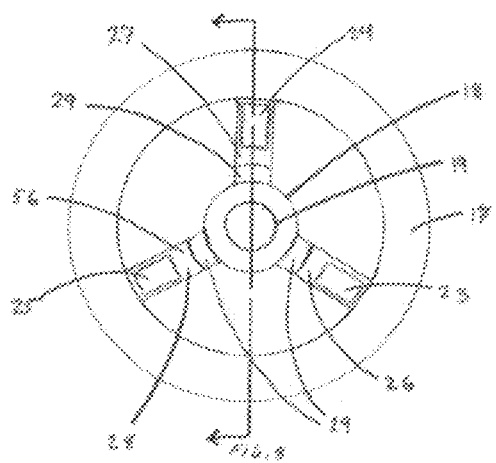
FIG. 7 shows a top view of a sensor assembly illustrating a taper constrain method.
Figure 8:
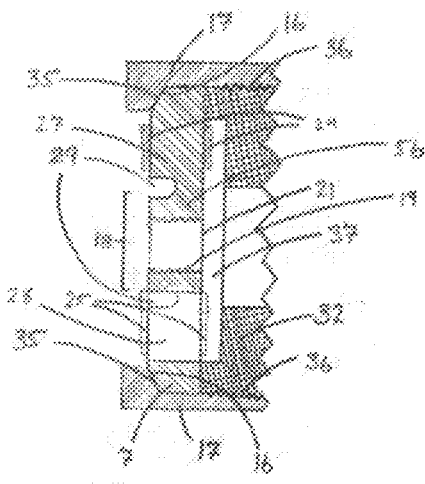
FIG. 8 shows a cross-section view of the sensor assembly of FIG. 7 further illustrating the taper constraint method.

FIG. 7 shows a top view of a sensor assembly employing a taper constrain method. FIG. 7 illustrates the following components:
  Metal base [56], which includes:
    Outer fixed portion [7] (FIG. 2A);

First flexural spoke [26], Second flexural spoke [27], and Third flexural spoke [28], each of which has formed in it:
Quasi-free boundary condition feature [29];
Inner sensing portion [18], in which is formed:
Ampoule connection location [19];
Constraint features [8] (FIG. 2A), which includes:
Locating male taper [16] (not specifically shown—shown in FIG. 8) in this alternate embodiment;
Securing features [10] (FIG. 2A), which comprises on the Metal base [56], which include:
Locating male taper [16] (not specifically shown—shown in FIG. 8) in this alternate embodiment;
While not a part of the Metal base [56], a Securing ring [17] engages with External threads [36] (FIG. 8) on the Adapter [32] (FIG. 8). The Locating male taper [16] on the Metal base [56] mates with the Locating female taper [35] on the Securing ring [17] to ensure concentricity between the Metal base [56] and the Adapter [32] (FIG. 8) by fully constraining the location with the mating taper and securing the assembly by clamping the Metal base [56] to the Adapter [32] (FIG. 8) which mounts to the jet injector housing in a preferred embodiment;
Sensor array [22] (not specifically labeled), which includes:
First strain sensor [23], Second strain sensor [24], and Third strain sensor [25];
This figure illustrates alternative Constraint features [8] and Securing features [10], which in this embodiment are one in the same, namely locating male taper [16].

FIG. 8 shows a cross-section view of the sensor assembly of FIG. 7 employing a taper a taper constraint method. FIG. 8 shows the following components:
Metal base [56], which includes:
Outer fixed portion [7];
Second flexural spoke [27], Third flexural spoke [28], and First flexural spoke [26] (not shown), each of which has formed in it:
Quasi-free boundary condition feature [29];
Inner sensing portion [18], in which is formed:
Ampoule connection location [19];
Piston pass-through port [21] so that the piston can connect to the actuator of a jet injector in a preferred embodiment;
Constraint features [8] (not specifically labeled), which includes:
Cross section view of Locating male taper [16] in this alternate embodiment;
Securing features [10] (not specifically labeled), on the Metal base [56], includes:
Locating male taper [16]
While not a part of the Metal base [56], a Securing ring [17] engages with External threads [36] on the Adapter [32]. The Locating male taper [16] on the Metal base [56] mates with the Locating female taper [35] on the Securing ring [17] to ensure concentricity between the Metal base [56] and the Adapter [32] by fully constraining the location with the mating taper and securing the assembly by clamping the Metal base [56] to the Adapter [32], which mounts to the jet injector housing in a preferred embodiment. Thus, the securing ring [17] and taper [16] on metal base [56] provide a self-centering feature.

Sensor array [22] (not specifically labeled), which includes:
Second strain sensor [24], Third strain sensor [25] and (First strain sensor [23] (not shown);
Adapter [32] in which has been formed:
Clearance space [37] so that the bottom strain sensors and required wiring have a space in which to occupy.
This figure illustrates in cross-section alternative Constraint features [8] and Securing features [10], which in this embodiment are one in the same.

Figure 9:
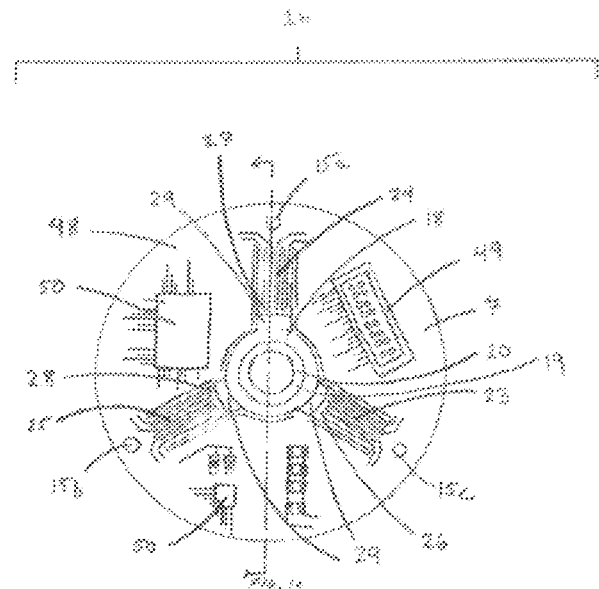
FIG. 9 shows a top view of a rigid one-part printed circuit board force sensor for a jet injector.

FIG. 9 shows a top view of a rigid single-part printed circuit board. FIG. 9 illustrates the following components:
Rigid one-part printed circuit board jet injector force sensor [1b], which includes:
Rigid single-part PCB base [48], which includes:
Outer fixed portion [7];
Inner sensing portion [18], onto which is mounted:
Threaded insert [20] which may be made of metal, polymer, or composite, in which is formed:
Ampoule connection location [19];
First flexural spoke [26], Second flexural spoke [27], and Third flexural spoke [28], each of which has formed in it:
Quasi-free boundary condition feature [29];
Constraint features [8] (not specifically labeled), which include constraint features and methods described earlier, for example with respect to FIGS. 2A, 2B, 3A or 3B, or other methods.
Securing features [10] (not specifically labeled), which include in this embodiment on the Rigid single-part PCB base [48]
Through hole one [15a], Through hole two [15b], and Through hole three [15c] through which
Bolt one [9a], Bolt two [9b], and Bolt three [9c] (none of which are shown, but see, e.g., FIG. 2B), connect the Rigid single-part PCB base [48], to the Adapter [32] (not shown, but see FIG. 2A) which mounts to the jet injector housing in a preferred embodiment.
Sensor array [22] (not specifically labeled), which includes:
First strain sensor [23], Second strain sensor [24], and Third strain sensor [25], represented as resistive strain gauge arrays in a preferred embodiment;
Connector [49] from which signals can be outputted from the sensor;
Integrated circuitry [50] which can perform, for example, processing, calibrating, mapping, and transmitting of raw data from the strain sensors.
The embodiment of FIGS. 9 and 10 presents a self-contained design that may only require power input and that can transmit the axial and lateral force data to be displayed on a visual, audible, or tactile feedback display, which is accomplished with a rigid one-part printed circuit board.

Figure 10:
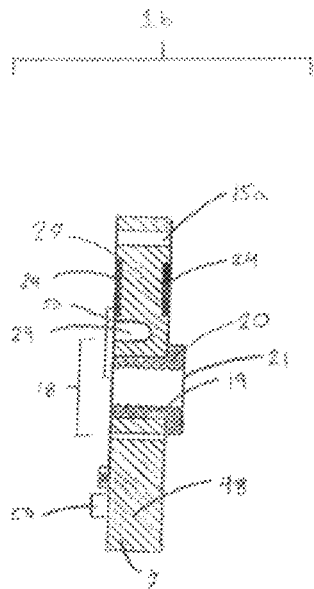
FIG. 10 shows a cross-section view of the rigid one-part printed circuit board jet injector force sensor of FIG. 9.

FIG. 10 shows a cross-section view of a rigid single-part printed circuit board of FIG. 9. FIG. 10 illustrates the following components:
Rigid one-part printed circuit board jet injector force sensor [1b], which includes:
Rigid single-part PCB base [48], which includes:
Outer fixed portion [7];
Inner sensing portion [18], onto which is mounted:
Threaded insert [20] which may be made of metal, polymer, or composite, in which is formed:

Ampoule connection location [19];
Piston pass-through port [21] so that the piston can connect to the actuator of a jet injector in a preferred embodiment;
Second flexural spoke [27], First flexural spoke [26] (not shown) and Third flexural spoke [28] (not shown), each of which has formed in it:
Quasi-free boundary condition feature [29];
Constraint features [8] (not specifically labeled), which include constrain features and methods described earlier, for example, with respect to FIGS. 2A, 2B, 3A or 3B, or other methods;
Securing features [10] (not specifically labeled), which include in this embodiment on the Rigid single-part PCB base [48]
Through hole one [15a], Through hole two [15b], and Through hole three [15c], of which a cross section view of Through hole one [15a] is shown, through which;
Bolt one [9a], Bolt two [9b], and Bolt three [9c] (not shown), connect the Rigid single-part PCB base [48] to the Adapter [32] (not shown, but see FIGS. 2A and 2B) which mounts to the jet injector housing in a preferred embodiment;
Sensor array [22] (not specifically labeled), which includes:
Second strain sensor [24], First strain sensor [23] and Third strain sensor [25] (not shown);
Integrated circuitry [50] which can, for example, perform processing, calibrating, mapping and transmitting raw data from the strain sensors.

Figure 11:
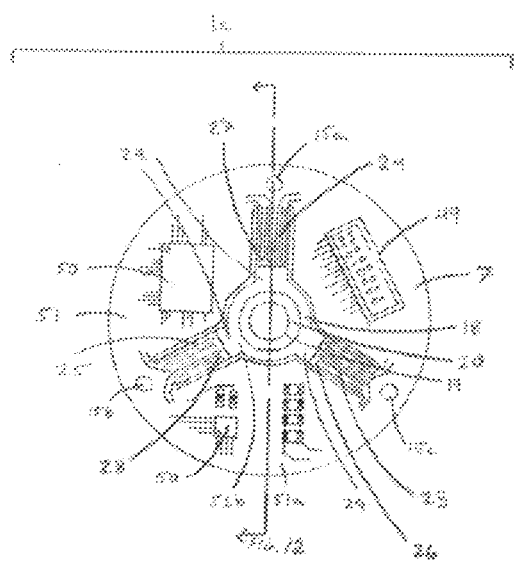
FIG. 11 shows a top view of a rigid two-part printed circuit board force sensor for a jet injector.

FIG. 11 shows a top view of a rigid two-part printed circuit board. FIG. 11 illustrates the following components;
Rigid two-part printed circuit board jet injector force sensor [1c], which includes:
Rigid two-part PCB base [51], which includes:
Rigid top-part PCB substrate [51a] and Rigid bottom-part PCB substrate [51b] (shown more distinctly in FIG. 12) which are joined together at Connection interface [52] with, for example, adhesive or solder, and which (when combined) includes:
Outer fixed portion [7];
Inner sensing portion [18], onto which is mounted:
Threaded insert [20] which may be made of metal, polymer, or composite, in which is formed:
Ampoule connection location [19];
First flexural spoke [26], Second flexural spoke [27], and Third flexural spoke [28], each of which has formed in it:
Quasi-free boundary condition feature [29];
Constraint features [8] (not specifically labeled), which includes: constraint features and methods described earlier, such as with respect to FIGS. 2A, 2B, 3A or 3B, or other suitable methods;
Securing features [10] (not specifically labeled), which includes in this embodiment on the Rigid two-part PCB base [51]
Through hole one [15a], Through hole two [15b], and Through hole three [15c] through which;
Bolt one [9a], Bolt two [9b], and Bolt three [9c] (none of which are shown), connect the Rigid two-part PCB base [51] to the Adapter [32] (not shown, but see FIG. 2A) which mounts to the jet injector housing in a preferred embodiment.

Sensor array [22] (not specifically labeled), which includes:
First strain sensor [23], Second strain sensor [24], and Third strain sensor [25], represented as resistive strain gauge arrays in a preferred embodiment;
Connector [49] from which signals can be outputted from the sensor;
Integrated circuitry [50] which can perform, for example, processing, calibrating, mapping, and transmitting raw data from the strain sensors.

Figure 12:
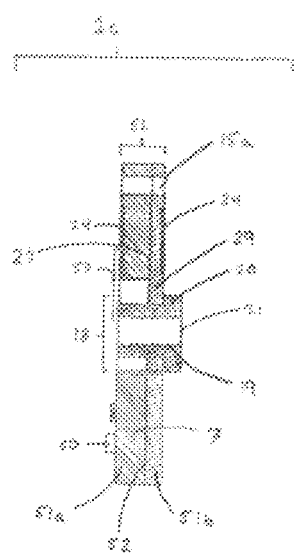
FIG. 12 shows a cross-section view of the rigid two-part printed circuit board force sensor of FIG. 11.

FIG. 12 shows a cross-section view of the rigid two-part printed circuit board of FIG. 11. FIG. 12 illustrates the following components:
Rigid two-part printed circuit board jet injector force sensor [1c], which includes:
Rigid two-part PCB base [51], which includes:
Rigid top-part PCB substrate [51a] and Rigid bottom-part PCB substrate [51b] which are joined together at Connection interface [52] with, for example, adhesive or solder, and which (when combined) comprise of:
Outer fixed portion [7];
Inner sensing portion [18], onto which is mounted:
Threaded insert [20] which may be made of metal, polymer, or composite, in which is formed:
Ampoule connection location [19];
Piston pass-through port [21] so that the piston can connect to the actuator of a jet injector in a preferred embodiment;
Second flexural spoke [27] First flexural spoke [26] (not shown) and Third flexural spoke [28] (not shown), each of which has formed in it:
Quasi-free boundary condition feature [29];
Constraint features [8] (not specifically labeled), which comprises of: constraint features and methods described earlier or other methods;
Securing features [10] (not specifically labeled), which includes in this embodiment on the Rigid two-part PCB base [51]
Through hole one [15a], Through hole two [15b], and Through hole three [15c], of which a cross section view of Through hole one [15a] is shown, through which;
Bolt one [9a], Bolt two [9b], and Bolt three [9c] (not shown), connect the Rigid two-part PCB base [51] to the Adapter [32] (not shown) which mounts to the jet injector housing in a preferred embodiment;
Sensor array [22] (not specifically labeled), which includes:
Second strain sensor [24] (shown in cross-section), First strain sensor [23] (not shown) and Third strain sensor [25] (not shown);
Integrated circuitry [50] which can, for example, perform processing, calibrating, mapping and transmitting raw data from the strain sensors.

The embodiment of FIGS. 11 and 12 presents a self-contained design that may only require power input and can transmit the axial and lateral force data to be displayed on a visual, audible, or tactile feedback display. The embodiment includes an assembly of two rigid PCB substrates joined together which eliminates the need, such as may be present in the Rigid single-part PCB base [48] of FIGS. 9 and 10, for further machining of the PCB substrate beyond machining the profile of the substrate. Instead, with the Rigid two-part PCB base [51], the Connection interface [52] can be covered with solder paste (presuming that both inner sides of each PCB substrate part have a metal coating), the parts can be aligned using a jig, and the entire assembly can be placed in a reflow oven. When cool, the solder has formed a secure bond between the upper and lower PCB substrate components.

Figure 13:
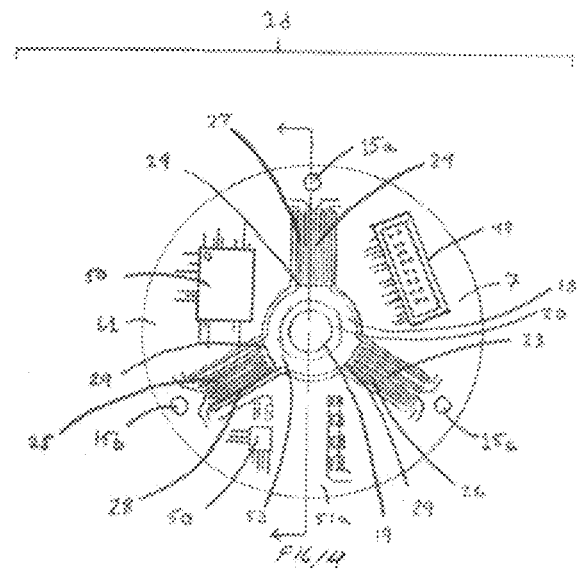
FIG. 13 shows a top view of a rigid two-part, flexible one-part printed circuit board force sensor for a jet injector.

FIG. 13 shows a top view of a two-part rigid, one-part flex printed circuit board sensor. FIG. 13 illustrates the following components;

Rigid two-part, flexible one-part flex printed circuit board jet injector force sensor [1d], which includes:
  Rigid two-part, flexible one-part PCB base [61], which includes:
    Rigid top-part PCB substrate [51a], Rigid bottom-part PCB substrate [51b] (not specifically shown), Center-part flex PCB substrate [53] (all shown more distinctly in FIG. 14) which are joined together at Upper connection interface [54a] and Lower connection interface [54b] with, for example, adhesive or solder, and which (when combined) includes:
      Outer fixed portion [7];
      Inner sensing portion [18], onto which is mounted:
        Threaded insert [20] which may be made of metal, polymer, or composite, in which is formed:
          Ampoule connection location [19];
        First flexural spoke [26], Second flexural spoke [27], and Third flexural spoke [28], each of which has formed in it:
          Quasi-free boundary condition feature [29];
      Constraint features [8] (not specifically labeled), which includes: constraints and methods described earlier with respect to FIGS. 2A-3B or other methods;
      Securing features [10] (not specifically labeled), which includes in this embodiment on the Rigid two-part, flexible one-part PCB base [61],
    Through hole one [15a], Through hole two [15b], and Through hole three [15c] through which;
      Bolt one [9a], Bolt two [9b], and Bolt three [9c] (none of which are shown, but see, e.g., FIG. 2A), connect the Rigid two-part, flexible one-part PCB base [61] to the Adapter [32] (not shown) which mounts to the jet injector housing in a preferred embodiment.
  Sensor array [22] (not specifically labeled), which includes:
    First strain sensor [23], Second strain sensor [24], and Third strain sensor [25], represented as resistive strain gauge arrays in a preferred embodiment;
  Connector [49] from which signals can be outputted from the sensor;
  Integrated circuitry [50] which can be used to perform processing, calibrating, mapping, and transmitting raw data from the strain sensors.

Figure 14:
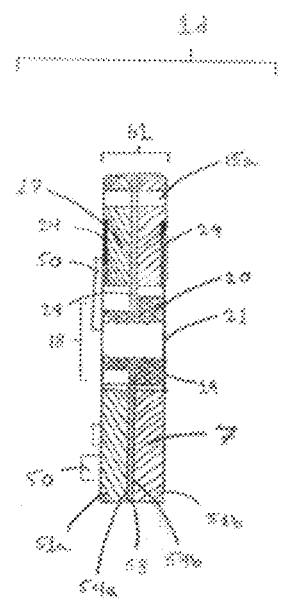
FIG. 14 shows a cross-section view of the rigid two-part, flexible one-part printed circuit board force sensor of FIG. 13.

FIG. 14 shows a cross-section view of the sensor of FIG. 13, including the two-part rigid, one part flex printed circuit board. FIG. 14 illustrates the following components:

Rigid two-part, flexible one-part flex printed circuit board jet injector force sensor [1d], which includes:
  Rigid two-part, flexible one-part PCB base [61], which includes:
    Rigid top-part PCB substrate [51a], Rigid bottom-part PCB substrate [51b] (not specifically shown), Center-part flex PCB substrate [53] which are joined together at Upper connection interface [54a] and Lower connection interface [54b] with, for example, adhesive or solder, and which (when combined) includes:
      Outer fixed portion [7];
      Inner sensing portion [18], onto which is mounted:
        Threaded insert [20] which may be made of metal, polymer, or composite, in which is formed:
          Ampoule connection location [19];
          Piston pass-through port [21] so that the piston can connect to the actuator of a jet injector in a preferred embodiment;
        Second flexural spoke [27] First flexural spoke [26] (not shown) and Third flexural spoke [28] (not shown), each of which has formed in it:
          Quasi-free boundary condition feature [29];
      Constraint features [8] (not specifically labeled), which includes: constraint features and methods described earlier, such as with respect to FIGS. 2A-3B, or other suitable features and methods;
      Securing features [10] (not specifically labeled), which includes in this embodiment on the Rigid two-part, flexible one-part PCB base [61]
    Through hole one [15a], Through hole two [15b], and Through hole three [15c], of which a cross section view of Through hole one [15a] is shown, through which;
      Bolt one [9a], Bolt two [9b], and Bolt three [9c] (not shown), connect the Rigid two-part, flexible one-part PCB base [61] to the Adapter [32] (not shown, but see FIG. 2A) which mounts to the jet injector housing in a preferred embodiment.
  Sensor array [22] (not specifically labeled), which includes:
    Second strain sensor [24] First strain sensor [23] (not shown) and Third strain sensor [25] (not shown);
  Integrated circuitry [50] which can, for example, be programmed or configured for processing, calibrating, mapping, and transmitting raw data from the strain sensors.

The embodiment of FIGS. 13 and 14 presents a self-contained design that may only require power input and can transmit the axial and lateral force data to be displayed on a visual, audible, or tactile feedback display. The embodiment includes an assembly of one flexible PCB substrate sandwiched between two rigid PCB substrates joined together which eliminates the need, such as may be present in the Rigid single-part PCB base [48] of FIG. 10, for further machining of the PCB substrate beyond machining its profile. Instead, with the Rigid two-part PCB base [51], the Upper and lower connection interfaces [54a and 54b, respectively] can be covered with solder paste (presuming that both inner sides of each rigid PCB substrates and both sides of the flexible PCB substrate have a metal coating). The parts can then be aligned using a jig and the entire assembly can be placed in a reflow oven. When cool, the solder has formed a secure bond between the layers.

Figure 15:
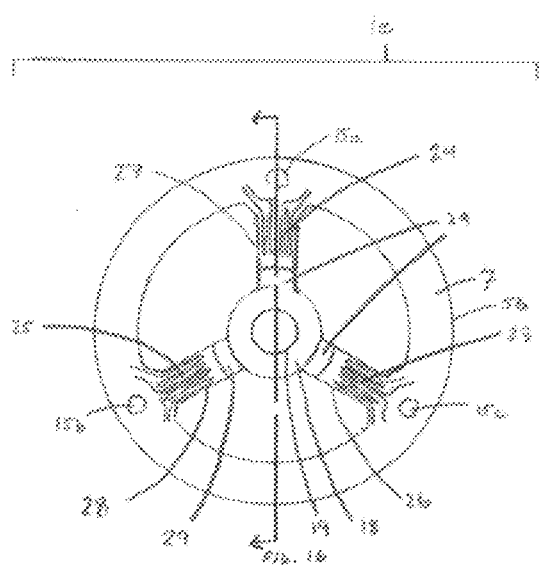
FIG. 15 shows a top view of a flexible two-part printed circuit board, aluminum base force sensor for a jet injector.
Figure 16:
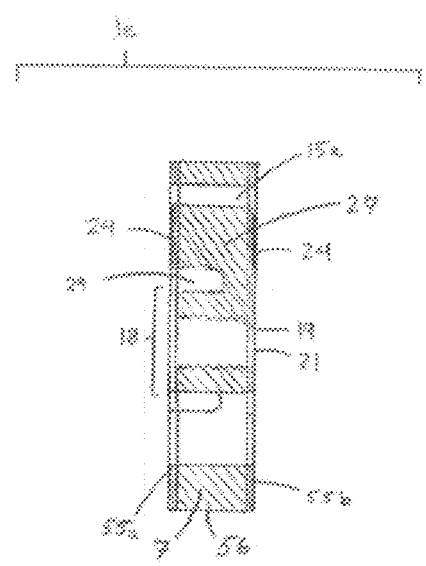
FIG. 16 shows a cross-section view of the flexible two-part printed circuit board, aluminum base force sensor of FIG. 15.

FIG. 15 shows a top view of a one-part flex, aluminum base printed circuit board force sensor. FIG. 15 illustrates the following components:

Flexible two-part printed circuit board, aluminum base jet injector force sensor [1e], which includes:
  Metal base [56], which includes:
    Outer fixed portion [7] (not specifically labeled);
    First flexural spoke [26], Second flexural spoke [27], and Third flexural spoke [28], of which a cross section view of First flexural spoke [26], and partial view of Third flexural spoke [28] are shown, both of which has formed in it:
Quasi-free boundary condition feature [29];
Inner sensing portion [18] (not specifically labeled), in which is formed:
Ampoule connection location [19];
Constraint features [8] (not specifically labeled), which includes: constraint features and methods described earlier, such as with respect to FIGS. 2A-3B, or other suitable features and methods;
Securing features [10] (not specifically labeled), which include on the Metal base [56]:
Through hole one [15a], Through hole two [15b], and Through hole three [15c];
Bolt one [9a], Bolt two [9b], and Bolt three [9c] (not shown) connect the Metal base [56] to the Adapter [32] (not shown) that mounts to the jet injector housing in a preferred embodiment.
Sensor array [22] (not specifically labeled), which includes:
Flexible top-part PCB substrate [55a], Flexible bottom-part PCB substrate [55b], in which are formed:
First strain sensor [23], Second strain sensor [24], and Third strain sensor [25], represented as resistive strain gauge arrays in a preferred embodiment;

FIG. 16 shows a cross-section view of the sensor of FIG. 15 including the two-part flex printed circuit board mounted on an aluminum base. FIG. 15 illustrates the following components:
Flexible two-part printed circuit board, aluminum base jet injector force sensor [1e], which includes:
Metal base [56], which includes:
Outer fixed portion [7] (not specifically labeled);
Cross-section view of the Second flexural spoke [27] First flexural spoke [26] (not shown) and Third flexural spoke [28] (not shown), each of which has formed in it:
Quasi-free boundary condition feature [29];
Inner sensing portion [18] (not specifically labeled), in which is formed:
Ampoule connection location [19];
Piston pass-through port [21] so that the piston can connect to the actuator of a jet injector in a preferred embodiment;
Constraint features [8] (not specifically labeled), which includes: constraint features and methods described earlier, such as with respect to FIGS. 2A-3B, or other suitable features and methods;
Securing features [10] (not specifically labeled), which includes in this embodiment on the two-part, flexible PCB mounted on aluminum base
Through hole one [15a], Through hole two [15b], and Through hole three [15c], of which a cross section view of Through hole one [15a] is shown, through which
Bolt one [9a], Bolt two [9b], and Bolt three [9c] (not shown), connect the Metal base [56] to the Adapter [32] (not shown) which mounts to the jet injector housing in a preferred embodiment;
Sensor array [22] (not specifically labeled), which includes:
Flexible top-part PCB substrate [55a], Flexible bottom-part PCB substrate [55b], in which are formed:
Second strain sensor [24], First strain sensor [23] (not shown) and Third strain sensor [25] (not shown);

The embodiment of FIGS. 15 and 16 presents a design that improves upon the above described embodiments using the Metal base [56] by requiring only two flexible PCB substrates containing the strain sensors to be mounted to the top and bottom of the Metal base [56], instead of 6 double-array strain sensor pads, which in previous embodiments are resistive strain gauges.

Figure 17:
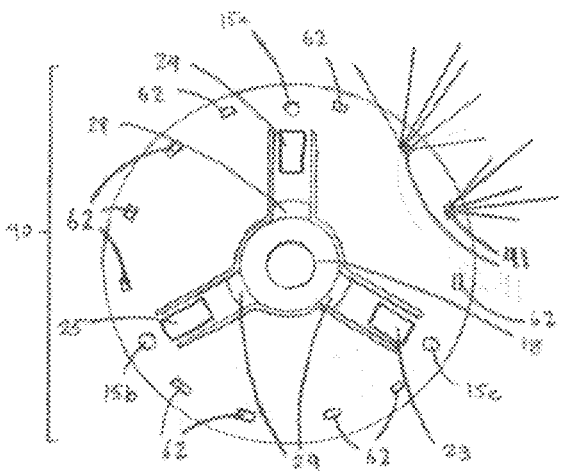
FIG. 17 shows a top view of an on-board visual feedback system to guide the user to minimize lateral forces on the nozzle.

FIG. 17 shows a top view of an on-board visual feedback system to guide the user to minimize lateral forces on the nozzle. The figure illustrates:
Circumferential array [40] which includes LEDs in a preferred embodiment that illuminate when the lateral forces exceed a pre-determined threshold to guide the user in reducing these lateral forces. The circumferential array [40] includes:
Illuminated LED [41] and Non-illuminated LED [62]. These LEDs may point down towards the surface receiving injection, tangentially to the surface receiving injection, or away from the surface receiving injection.
The other components shown in FIG. 17 have been described above, for example, in reference to FIGS. 9, 11, 13 and 15.

Figure 18:
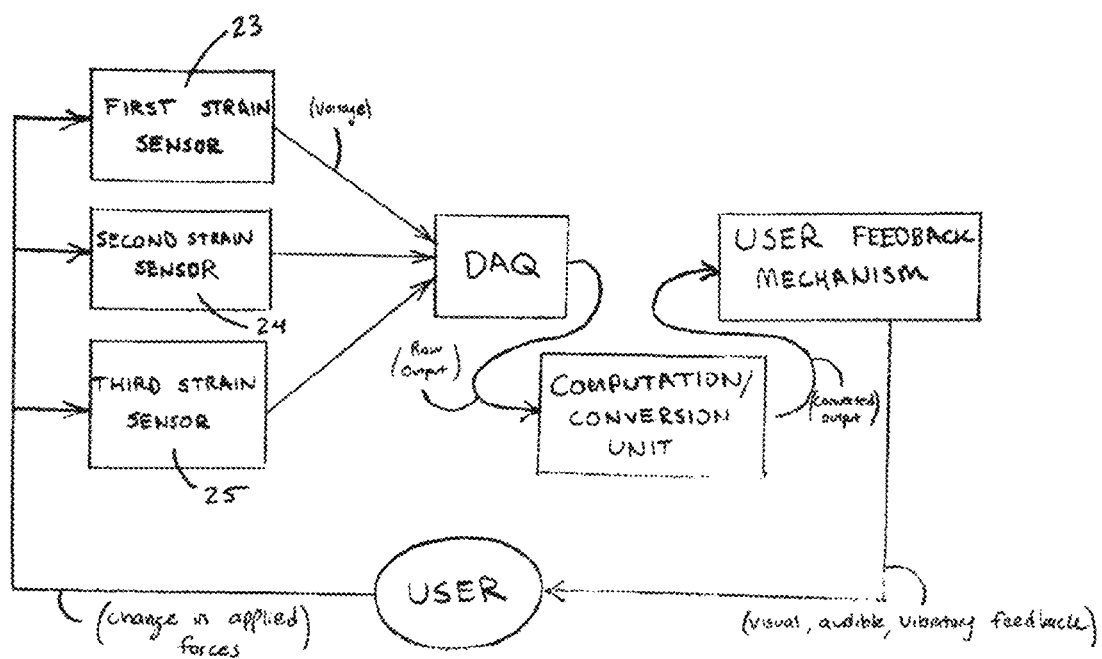
FIG. 18 shows a schematic diagram of a feedback loop between the user and the multi-axis low-displacement force sensor.

FIG. 18 shows a schematic diagram of a feedback loop between the user and the multi-axis low-displacement force sensor. This figure shows an embodiment of possible data flow in the system, for example, occurring onboard, in an integrated PCB design, or on a remote data acquisition (DAQ) board located elsewhere on the device or located off the device completely.

Figure 19:
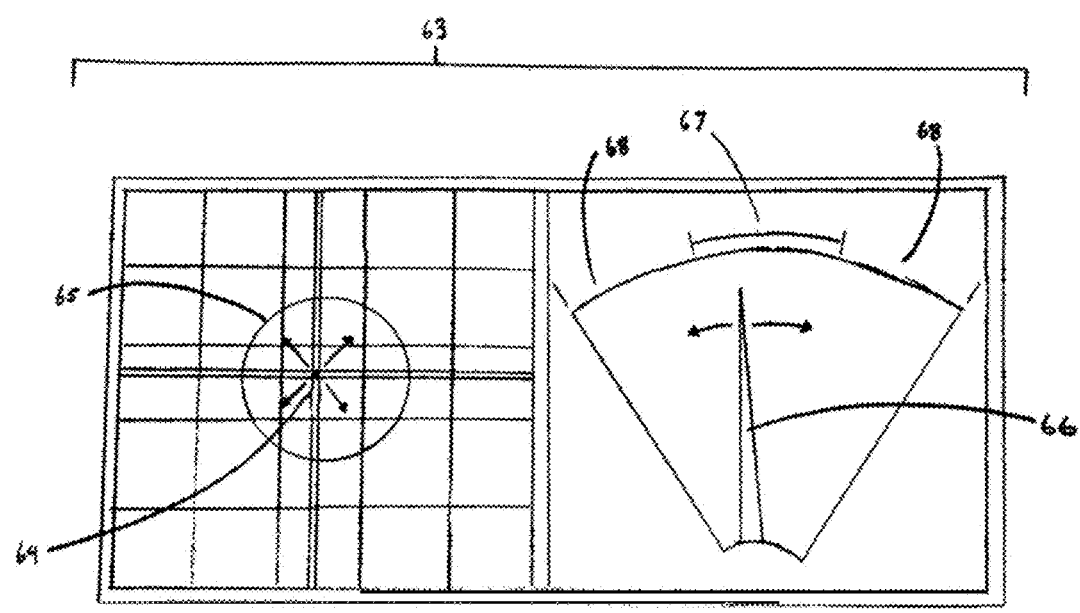
FIG. 19 shows a view of a lateral and axial force display suitable for showing on a screen integrated with a jet injector or on a separate monitor.

FIG. 19 shows a view of a visual feedback method that may be shown on a screen integrated with the jet injector or on a separate monitor. This figure shows an embodiment of a visual feedback method for communicating to the user the lateral and axial forces applied to the nozzle. The Lateral and axial force display [63] includes:
Left hand side display which displays a Lateral force cursor [64] to indicate the amount of lateral force applied to the nozzle. A threshold drawn as a circle [65] allows for the user to see graphically if the lateral forces fall within a pre-determined appropriate range.
Right hand side display which displays an Axial force indicator [66] to indicate the amount of axial force applied into the nozzle. Appropriate force level range [67] and inappropriate force level range [68] are displayed and can be compared against the current force level displayed by the Axial force indicator [66]. It is also possible to combine the left hand and right hand displays into a single display. For example, the single display may be similar to the left side display, in that lateral forces are represented as distances from a 0,0 origin in the plane, but axial forces may be represented by colors (e.g., orange for under force range, green for in force range, and red for over force range).

The feedback systems and methods described above may also include a lock-out feature, whereby the user is prevented from initiating or continuing injection until the forces applied to the nozzle are within an acceptable range.

Figure 20:
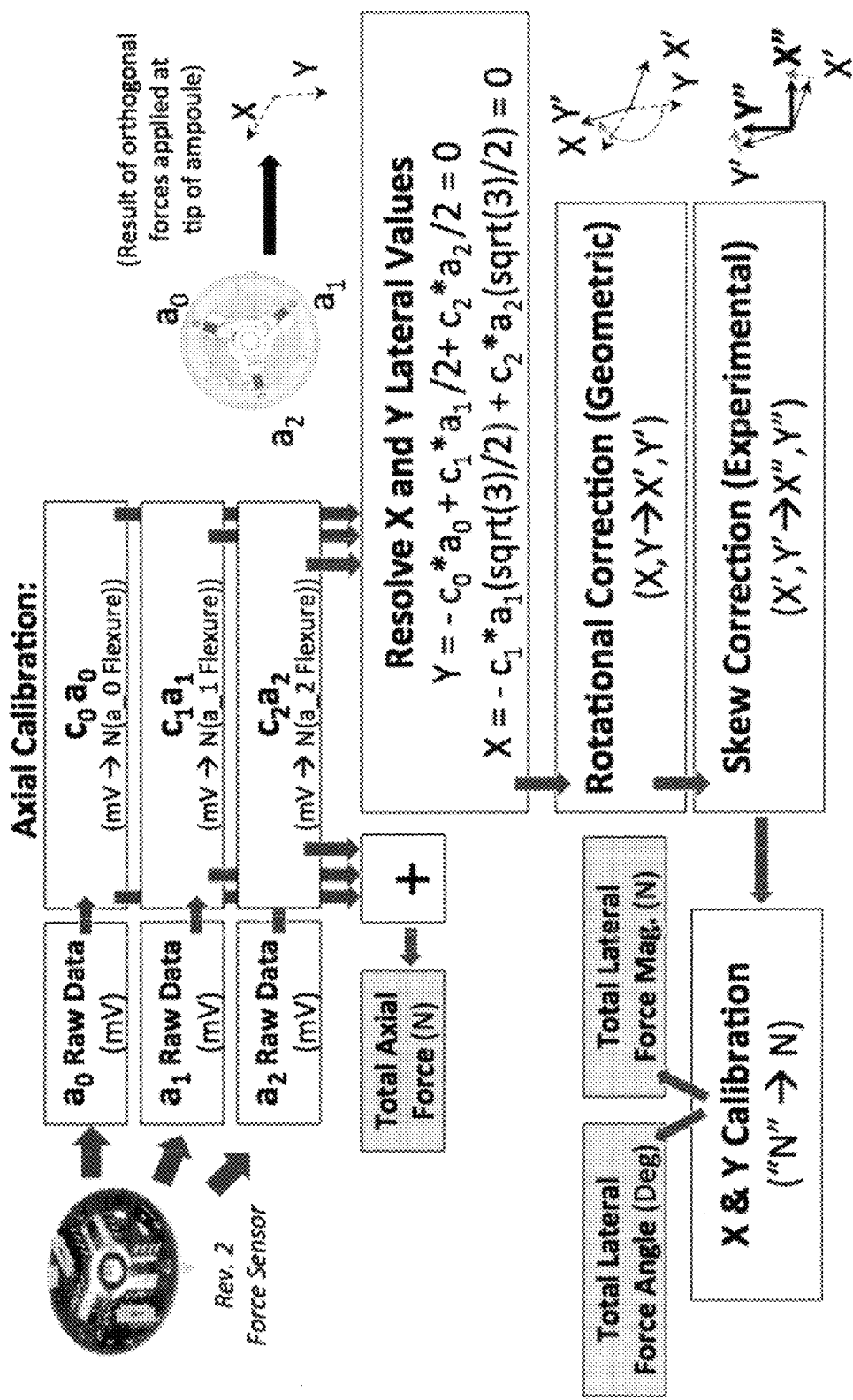
FIG. 20 is a schematic flow chart illustrating a process of resolving axial force and lateral force magnitude and angle using data obtained from a force sensor of the present invention.

FIG. 20 is a schematic flow diagram illustrating a system and process for measuring axial force and resolving lateral forces using data obtained from a force sensor of the present invention. The various inputs, outputs and processing blocks of the system and process will be described.

Blocks labeled "RAW DATA": The system first reads the raw voltage in mV from the 3 full bridge strain gauge arrays that are each mounted on one of the 3 flexures of the force sensor.

Blocks labeled "AXIAL CALIBRATION": Three linear coefficients found experimentally for each of the 3 strain gauges multiply the raw voltage in mV and convert the measurements into a force supported by each flexure in N.

Block labeled "TOTAL AXIAL FORCE": The total axial force is found by summing the 3 force measurements from the 3 full bridge strain gauge arrays and subtracting the average measured nominal force when no external forces are applied. If a load vector is truly axial with no lateral components, the load on each flexure is ⅓ the total axial force.

Block labeled "RESOLVE X AND Y LATERAL DATA": Next, using pre factors based on trigonometry, the presumption that only vertical bending forces are measured, and the presumption that the amount of vertical bending is linearly related to the magnitude of the lateral force (all of which are true at small deflections), it is possible to resolve unscaled representations of the X and Y lateral forces using combinations of the values measured from the 3 full bridge strain gauge arrays using the equations shown. The measured values $a_0$, $a_1$, and $a_2$ in this case already contain the pre factors from the axial calibration in an effort to normalize them with each other.

Pre factors are coefficients. In the case of the "pre factors" for $a_0$, $a_1$, and $a_2$, the pre factors are calibration coefficients which convert mV to N (assuming a linear relationship). In the case of trigonometric pre factors, each factor is a trig coefficient that is converting the force along the hypotenuse to a force in the x or y direction for a given angle.

Block labeled "ROTATIONAL CORRECTION (GEOMETRIC)": This procedure takes the rotation matrix (with theta given as an angle between the x axis of the sensor and desired device x axis):

[cos (theta) sin (theta)
−sin (theta) cos (theta)]

times the unscaled force vector

[X, Y]

to get the geometric rotational corrected unscaled force vector

[X', Y']

This provides correction if a force sensor's X and Y axes are not physically aligned with the rest of the device.

Block labeled "SKEW CORRECTION (EXPERIMENTAL)": This procedure corrects for skew in the axes which can arise from a number of sources, such as due to the normalization detailed in the "Resolve X and Y Lateral Data" procedure, which is close but not an exact normalization for the lateral force measurements.

Here, we find angles a and b, where a is the angle between the measured and desired y axes (or Y' and Y", respectively) and b is the angle between the measured and desired x axes (or X' and X", respectively). We look to eliminate angles a and b such that the measured X and Y forces are indeed orthogonal.

We then say that the skew matrix (with a and b defined above) is:

[1 −tan(a)
−tan(b) 1+(tan(a)*tan(b))]

times the geometric rotational corrected unscaled force vector

[X', Y']

gives the experimentally skewed rotational corrected unscaled force vector

[X", Y"]

Block labeled "X & Y CALIBRATION": In this procedure, 2 linear coefficients found experimentally multiply the X" and Y" raw values (which report the value of force in fake units of force ("N")) to get the true values of lateral force X and Y reported in N. Average offsets measured when no external forces are applied are subtracted from the measured value to properly zero the measurement. The final X and Y measurements can then be transformed into a lateral force vector, which has a magnitude and angle.

In matrix operation, the axial force $F_{AXIAL}$ can be expressed as:

$$F_{AXIAL} = \begin{bmatrix} c_0 & c_1 & c_0 \end{bmatrix} \begin{bmatrix} a_0 \\ a_1 \\ a_0 \end{bmatrix}$$

and the lateral force components $F_X$ and $F_Y$ can be expressed as:

$$\begin{bmatrix} F_X \\ F_Y \end{bmatrix} = \begin{bmatrix} L_X & 0 \\ 0 & L_Y \end{bmatrix} \begin{bmatrix} 1 & -\tan(a) \\ -\tan(b) & 1+\tan(a)\tan(b) \end{bmatrix} \begin{bmatrix} \cos(\theta) & \sin(\theta) \\ -\sin(\theta) & \cos(\theta) \end{bmatrix}$$

$$\begin{bmatrix} 0 & -\frac{\sqrt{3}}{2} & \frac{\sqrt{3}}{2} \\ -1 & \frac{1}{2} & \frac{1}{2} \end{bmatrix} \begin{bmatrix} c_0 & 0 & 0 \\ 0 & c_1 & 0 \\ 0 & 0 & c_2 \end{bmatrix} \begin{bmatrix} a_0 \\ a_1 \\ a_0 \end{bmatrix}$$

where $c_0$, $c_1$, $c_2$, $L_x$, $L_y$, a and b are all determined by experimental calibration, theta is determined by geometry, and $a_0$, $a_1$ and $a_2$ are measured.

FIG. 21 is diagram illustrating the lateral force theoretical framework, including an example force sensor, forces on the tip of an ampoule, and associated force equations. The figure is a more detailed illustration of the procedure of the Block labeled "Resolve X and Y Lateral Data" of FIG. 20.

In FIG. 21, on the left, a top down view of the force sensor is shown with the center lines of each flexure indicated, spaced equally 120 degrees apart. In the middle and on the right, three scenarios are shown. The scenarios include, from top to bottom, one where no lateral force is applied, one where only a lateral force in the Y direction is applied, and one where only a lateral force in the X direction is applied to the tip of the ampoule in the direction of the bolded arrows. The equations shown in each box represent the theoretical model built to resolve the lateral forces (based on trigonometry), where "X" and "Y" represent an unscaled value for the lateral forces (which, would also need to be corrected for skew and geometric factors).

In the first scenario where no lateral force is applied to the tip of the ampoule (but a normal force may be applied), $a_0$, $a_1$, and $a_2$ (the differential voltage measurements from each full bridge strain gauge mounted on the 3 flexures) are at some value. When the axial force calibration is applied, i.e., the experimentally derived factors ($c_0$, $c_1$, and $c_2$) for each flexure are multiplied by the raw data ($a_0$, $a_1$, and $a_2$) to convert mV to N supported by that bridge, the values from the 3 flexures are equal. Indeed, when equal quantities for $c_0{*}a_0$, $c_1{*}a_1$, and $c_2{*}a_2$ are substituted into the equations for lateral force values in the x and y directions, the output is 0 in both X and Y lateral directions. If an axial force is superimposed on top of these values, the equations still yield 0 as the model is constructed such that that purely lateral applied forces do not effect purely axial force measurements and vice versa.

In the second scenario where a lateral force in the Y direction is applied to the tip of the ampoule, all arrays are loaded and output some non-zero measurement due to the lateral force application. It is assumed that, because of symmetry, the $a_1$ and $a_2$ flexures measure equal values of bending in the vertical direction due to the lateral loading and reject all torsion, side bending, or overall compression due to the lateral loading (because of the full bridge strain gauge configuration employed in this sensor), and therefore $c_1*a_1$, and $c_2*a_2$ are equal. It is assumed that, again because of symmetry, the $a_0$ flexure exhibits only vertical bending due to lateral loading and no torsion, side bending or compression due to lateral loading (although these latter three would be rejected anyway for the same reason as above). Therefore, when the equations are applied, the equations indeed resolve a non-zero value in the Y direction and 0 in the X direction. Again, if an axial force is superimposed on top of these values, the equations still yield the same results.

In the third scenario where a lateral force in the X direction is applied to the tip of the ampoule, all arrays are put under load. However, it is assumed that the $a_0$ flexure is in torsion only and, therefore, does not register any vertical bending, side bending, or compression due to lateral loading; $c_0*a_0$ is at some nominal value. It is assumed that, because of symmetry, $c_1*a_1$, and $c_2*a_2$ values that are equal but opposite from the nominal value of $c_0*a_0$ because the $a_1$ flexure is forced upwards and the $a_2$ flexure is forced downwards. Again, it is assumed that all torsion, side bending, and compression of these flexures is rejected due to the full bridge strain gauge configuration employed. When the equations are applied, the equations indeed resolve a non-zero value in the X direction and 0 in the Y direction. Again, if an axial force is superimposed on top of these values, the equations still yield the same results.

From here, lateral forces not along either the X or Y axes can be constructed by combining the X and Y components derived above.

A search has identified the following prior art relating to force sensors:

US patent application publication 2012/0266694 A1 ("Multiaxial force-torque sensors") presents a configuration of strain gauges mounted only on one side of the flexures and utilizes flexures that have a fixed boundary condition at both ends. The former precludes the ability to employ a full bridge strain gauge array, which allows for the measurement of much smaller deflections. The latter requires that the strain sensors be confined to half of the length of the flexure in either a fully compressive or fully tensile zone to achieve maximum signal output, which means that the strain sensors are confined to half of the surface area on the top and bottom of the flexure. With this constraint, the flexures must be twice the length of the strain sensor for maximum signal output for a set flexure length.

U.S. Pat. No. 4,448,083 ("Device for measuring components of force and moment in plural directions") presents spokes with flexible sections to provide flexibility when loaded with a moment around the central axis. However, because only the width has been modified and not the depth when viewed from the top, the spokes would still present significant stiffness when loaded with a vertical force, normal to the top surface of the central hub. Because beam stiffness at any location is linearly related with width of the spoke and cubically related to height of the spoke, these cutouts are relatively inefficient at making the boundary condition behave more "free-like" versus "fixed-like" when loaded along the central axis, normal to the top surface of the central hub. In addition, the strain sensors are arranged on spokes that form a cruciform shape and the patent calls for strain sensors mounted on each spoke, which is both redundant and unnecessary.

U.S. Pat. No. 8,250,934 B2 ("Multi-Axis force sensor and acceleration sensor") describes a sensor that includes a flexure with "strain-generating portions" which are formed by varying the height of the flexure over its length. However, these features are formed merely to generate localized strain on the top surface of the device when the flexures are deformed and preclude the ability to mount strain sensors on the bottom surface. They are not designed to form a quasi-free boundary condition feature which is suitable for a full bridge strain gauge array. In addition, strain sensors are shown arranged on spokes that form a cruciform shape, which is both redundant and unnecessary.

U.S. Pat. No. 4,536,746 A ("Transducer for converting three-dimensional mechanical input displacements into a corresponding electrical output signal") describes a configuration of flexible members to convert displacement to electrical signals. While deflections to applied forces are necessary for an electro-mechanical sensor to output a signal, gross deflections would cause misalignment between the piston and the ampoule causing the piston to jam when actuated. In addition, the strain sensors are arranged on flexures that form a cruciform shape and the patent calls for strain sensors mounted on each flexure, which is both redundant and unnecessary. Further, a jet injector drug delivery ampoule assembly could not be mounted to such a sensor.

U.S. Pat. No. 4,862,751 A ("Force-detecting apparatus"), U.S. Pat. No. 5,889,214 A ("6-Component Load Cell"), and U.S. Pat. No. 4,905,523 A ("Force detector and moment detector using resistance element") describe a different configuration of flexible members again arranged in a cruciform shape. This configuration is both redundant and unnecessary. There are additionally a number of issues inherent with these cruciform shaped sensor arrays. The sensor described in U.S. Pat. No. 4,862,751 is overly complex, requiring a multitude of components which, when assembled, form a significant length which would be difficult to implement on the front of a jet injector. The sensor described in U.S. Pat. No. 5,889,214 requires small precision features to be formed into the sides and top of each flexure that would be difficult to manufacture. The sensor described in U.S. Pat. No. 4,905,523 also has fixed-fixed flexures, which limit the area on the top and bottom to which strain sensors can be mounted in fully compressive or fully tensile zones.

There are a few patents that describe multi-axis force sensors not designed specifically in a cruciform shape. U.S. Pat. No. 4,836,034 A ("Force Sensing Apparatus") describes a sensor formed by circular holes cut around a circumference with strain sensors mounted on the thin bridges between circular holes. However, sensing elements are formed on one planar surface, precluding the ability to utilize sensing elements on both the top and bottom of the deflecting structure to measure smaller deflections. In addition, eight or a multiple of 8 holes are placed circumferentially around the center, requiring the total number of sensing elements to be at least 16, which is redundant and unnecessary. U.S. Pat. No. 4,763,531 A ("Force-Torque Sensor") describes a sensor configuration whereby a full bridge resistive strain gauge sensor array is employed on at least three flexures. However, this is employed on two identical assemblies mounted on top of one another. The dual assemblies are designed to measure torque as well as force, all of which may not be required in the application to jet injectors. In addition, no quasi-free boundary condition elements have been formed into the flexure, meaning that the flexures must be twice the length of the strain sensors so that said sensors can be placed in fully compressive or fully tensile zones to maximize signal output.

There is a multitude of multi-axis force sensors formed in printed circuitry boards. U.S. Pat. No. 6,951,142 B2 ("Six-axis force sensor chip and six-axis force sensor using the same"), U.S. Pat. No. 7,536,923 B2 ("Force Sensor Chip"), and U.S. Pat. No. 5,263,375 A ("Contact detector using resistance elements and its application") are formed in a cruciform shape, which, as described earlier, is unnecessary and redundant. In addition, these sensors are formed in such a way that the deflection for a given force is very large due to a network of flexing elements. An extreme example of a design which would lead to severe deformations is illustrated in U.S. Pat. No. 7,490,524 B2 ("Force Sensor Chip").

There are, moreover, a plethora of multi-axis force sensors that have been designed for pointing or inducing virtual motion within a computer environment or for a joystick to regulate electro-mechanical systems. These appear to focus on user input as a means to control systems. Patents in this realm include U.S. Pat. No. 6,243,077 ("Sensor and circuit architecture for three-axis strain gauge pointing device and force transducer"), U.S. Pat. No. 4,680,577 ("Multipurpose cursor control keyswitch"), U.S. Pat. No. 5,640,178 A ("Pointing Device"), U.S. Pat. No. 7,409,879 ("Construction machine comprising a joystick control"), U.S. Pat. No. 5,854,622 A ("Joystick apparatus for measuring handle movement with six degrees of freedom"), U.S. Pat. No. 6,246,391 B1 ("Three-dimensional tactile feedback computer input device"), U.S. Pat. No. 6,681,880 B2 ("Control Lever").

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

A list of parts is attached as Appendix A.

What is claimed is:

1. A device for measuring forces and/or torques, the device comprising:
    two or more flexural spokes, each having upper and lower surfaces,
    two or more strain sensors formed on the upper and lower surfaces of said flexural spokes,
    a fixed rim, for providing a connection to the device,
    a sensing hub, for inputting said forces and/or torques,
    a modified boundary constraint on the spoke, for increasing the surface area occupied by fully compressive zones and fully tensile zones which occur on the top and bottom or vice versa on any or all of said flexural spokes when said forces and/or torques are applied to the sensing hub, and
    said spokes connect said fixed rim to said sensing hub.

2. The device of claim 1 wherein the fixed rim, flexural spokes, and sensing hub are of a rigid material.

3. The device of claim 2 wherein the modified boundary constraint of the flexural spoke is attained by forming a cutout in the base material, as seen from the side profile.

4. The device of claim 2 wherein the modified boundary constraint of the flexural spoke is attained by a member with high flexibility in the vertical direction (versus horizontal direction) connecting each flexural spoke to the sensing hub.

5. The device of claim 2 wherein strain sensors are formed of full-bridge resistive strain gauge arrays.

6. The device of claim 2 wherein strain sensors are formed of semiconductor strain sensors.

7. A method of measuring forces and/or torques, the method comprising:
    providing two or more flexural spokes, each having upper and lower surfaces, sensing strain by two or more strain sensors formed on the upper and lower surfaces of said flexural spokes,
    connecting, by said flexural spokes, a fixed rim to a sensing hub to which said forces and/or torques are applied,
    modifying the boundary constraints on the spoke, to increase the surface area occupied by fully compressive zones and fully tensile zones which occur on the top and bottom or vice versa on any or all of said flexural spokes when said forces and/or torques are applied to the sensing hub.

8. The method of claim 7 wherein the sensing assembly is formed of individual resistive strain gauges formed in flexible printed circuit board material fixed to a metal base material.

9. The method of claim 7 wherein the sensing assembly is formed of a metal base material and two sheets of flexible printed circuit board material, in which are formed resistive strain gauges that are mounted to the upper and lower surface of the metal base material.

10. The method of claim 7 wherein the sensing assembly is formed of a single piece of rigid printed circuit board material, in which are formed resistive strain gauges on upper and lower surfaces.

11. The method of claim 7 wherein the sensing assembly is formed of two separate pieces of rigid printed circuit board material, in which are formed resistive strain gauges on one side, the pieces being connected to each other in a later process.

12. The method of claim 7 wherein the sensing assembly is formed of two separate pieces of rigid printed circuit board material, in which are formed resistive strain gauges on one side, and one piece of flexible printed circuit board, all of which are connected to each other in a later process.

13. A needle-free injector, comprising:
    a) an ampoule including a nozzle and a piston movable within the ampoule;
    b) a controllable actuator coupled to the piston to drive the piston to eject a substance through the nozzle; and
    c) a force sensor between the ampoule and a housing of the actuator, the force sensor comprising:
        i) a sensing hub coupled to the ampoule;
        ii) a fixed rim coupled to the actuator;
        iii) flexural spokes connecting the fixed rim to the sensing hub;
        iv) strain gauges placed at the spokes to measure strain, from which forces at the nozzle are calculated.

14. The force sensor of claim 13, wherein the sensing hub and fixed rim are concentric rings.

15. The force sensor of claim 14, wherein the sensing hub includes a port through which the piston extends.

16. The force sensor of claim 15, wherein the force sensor includes three flexural spokes.

17. The force sensor of claim 16, wherein the flexural spokes are radially symmetric.

18. The force sensor of claim 13, wherein each of the flexural spokes includes a modified boundary constraint.

19. The force sensor of claim 18, wherein each flexural spoke includes a top surface and a bottom surface and wherein a portion of the strain gauges is placed at the top surfaces of the spokes and the remaining portion of the strain gauges is placed at the bottom surfaces of the spokes.

20. The force sensor of claim 19, wherein the modified boundary constraint of each spoke is formed near the sensing hub.

21. The force sensor of claim 20, wherein, at each spoke, the strain gauges are arranged in a full bridge strain gauge array.

22. The force sensor of claim 13, wherein the fixed rim, flexural spokes, and sensing hub are integrally formed from a substrate.

23. The force sensor of claim 22, wherein the strain gauges are formed in printed circuit board.

24. The force sensor of claim 23, wherein the substrate is metal and the strain gauges are attached to the substrate.

25. The force sensor of claim 23, wherein the substrate is the printed circuit board in which the strain gauges are formed.

26. The force sensor of claim 13, wherein the fixed rim, flexural spokes, and sensing hub are formed from multiple substrates that are bonded together.

27. The force sensor of claim 26, wherein the substrates include flexible and rigid substrates including any combination of printed circuit boards, metal substrates and polymer substrates.

28. The needle-free injector of claim 13, wherein the sensor further includes circuitry coupled to the strain gauges to perform at least one of processing, calibrating, mapping and transmitting strain data.

29. The needle-free injector of claim 13, further including an element to provide an indication of the calculated forces.

30. The needle-free injector of claim 29, wherein the element is a display that provides magnitude and direction of the calculated forces.

31. The needle-free injector of claim 30, wherein the display includes light-emitting diodes placed at the fixed rim of the force sensor.

32. The needle-free injector of claim 30, wherein the display is projected onto the surface being injected.

33. The needle-free injector of claim 30, wherein the display is remote from the force sensor.

34. A force sensor for a needle-free injector, the sensor comprising:
   a) a sensing hub to couple to an ampoule of the needle-free injector;
   b) a fixed rim to couple to an actuator of the needle-free injector;
   c) flexural spokes connecting the sensing hub and fixed rim, each of the spokes having a modified boundary constraint; and
   d) strain gauges placed at the spokes, from which forces at a nozzle of the ampoule are calculated.

35. The sensor of claim 34, wherein the modified boundary constraint is a notch in the spoke.

36. The sensor of claim 35, wherein the modified boundary constraint is formed near the sensing hub.

37. The sensor of claim 36, wherein the sensing hub and fixed rim are concentric rings.

38. The sensor of claim 37, wherein the flexural spokes are radially symmetric.

39. The sensor of claim 38, wherein the sensor includes three flexural spokes spaced 120 degrees apart.

40. The sensor of claim 34, wherein each flexural spoke has a constant width along a length of the spoke.

41. The sensor of claim 34, wherein each flexural spoke includes a top surface and bottom surface and wherein a portion of the strain gauges is placed at the top surfaces of the spokes and the remaining portion of the strain gauges is placed at the bottom surfaces of the spokes.

42. The sensor of claim 34, wherein, at each spoke, the strain gauges are arranged in a full bridge strain gauge array.

43. The sensor of claim 34, wherein the fixed rim, flexural spokes, and sensing hub are integrally formed from a substrate.

44. The sensor of claim 43, wherein the strain gauges are formed in printed circuit board.

45. The sensor of claim 43, wherein the substrate is metal and the strain gauges are attached to the substrate.

46. The sensor of claim 44, wherein the substrate is the printed circuit board in which the strain gauges are formed.

47. The sensor of claim 35, wherein the fixed rim, flexural spokes, and sensing hub are formed from multiple substrates that are bonded together.

48. The sensor of claim 47, wherein the substrates include flexible and rigid substrates including any combination of printed circuit boards, metal substrates, and polymer substrates.

49. The sensor of claim 34, further including circuitry coupled to the strain gauges to perform at least one of processing, calibrating, mapping and transmitting strain data.

* * * * *